US010512389B2

(12) United States Patent
Shiraki et al.

(10) Patent No.: US 10,512,389 B2
(45) Date of Patent: Dec. 24, 2019

(54) IMAGE PROCESSING DEVICE, IMAGE PROCESSING METHOD, AND ENDOSCOPE SYSTEM

(71) Applicant: SONY CORPORATION, Tokyo (JP)

(72) Inventors: Hisakazu Shiraki, Kanagawa (JP); Koji Kashima, Kanagawa (JP); Toru Mitome, Tokyo (JP)

(73) Assignee: SONY CORPORATION, Tokyo (JP)

( * ) Notice: Subject to any disclaimer, the term of this patent is extended or adjusted under 35 U.S.C. 154(b) by 127 days.

(21) Appl. No.: 15/539,859

(22) PCT Filed: Jan. 4, 2016

(86) PCT No.: PCT/JP2016/050016
§ 371 (c)(1),
(2) Date: Jun. 26, 2017

(87) PCT Pub. No.: WO2016/114155
PCT Pub. Date: Jul. 21, 2016

(65) Prior Publication Data
US 2017/0367560 A1 Dec. 28, 2017

(30) Foreign Application Priority Data
Jan. 13, 2015 (JP) ................. 2015-004127

(51) Int. Cl.
*A61B 1/00* (2006.01)
*A61B 1/04* (2006.01)
(Continued)

(52) U.S. Cl.
CPC ............ *A61B 1/00009* (2013.01); *A61B 1/00* (2013.01); *A61B 1/00087* (2013.01);
(Continued)

(58) Field of Classification Search
CPC ............ A61B 1/00009; A61B 1/00193; A61B 1/00087; A61B 1/00; A61B 1/04; H04N 13/128; H04N 13/204
(Continued)

(56) References Cited

U.S. PATENT DOCUMENTS

2003/0083551 A1* 5/2003 Takahashi .......... A61B 1/00193
600/166
2010/0053308 A1 3/2010 Namii et al.
(Continued)

FOREIGN PATENT DOCUMENTS

JP 3869029 B2 1/2007
JP 2010-0057619 A 3/2010
(Continued)

OTHER PUBLICATIONS

International Search Report and Written Opinion of PCT Application No. PCT/JP2016/050016, dated Mar. 15, 2016, 02 pages of English Translation and 07 pages of ISRWO.

*Primary Examiner* — Amandeep Saini
(74) *Attorney, Agent, or Firm* — Chip Law Group

(57) ABSTRACT

The present technology relates to an image processing device, an image processing method, a program, and an endoscope system that can reduce a burden on a user. A parallax amount adjustment unit adjusts the parallax amount of a three-dimensional (3D) biological image of an imaged living organism, depending on whether the parallax of the 3D biological image puts a burden on a user. The present technology can be applied to an endoscope system or the like that captures an image of a living organism with an endoscope, for example.

21 Claims, 17 Drawing Sheets

(51) Int. Cl.
*H04N 13/128* (2018.01)
*H04N 13/204* (2018.01)

(52) U.S. Cl.
CPC ............ *A61B 1/00193* (2013.01); *A61B 1/04* (2013.01); *H04N 13/128* (2018.05); *H04N 13/204* (2018.05)

(58) Field of Classification Search
USPC ......................................................... 382/100
See application file for complete search history.

(56) References Cited

U.S. PATENT DOCUMENTS

| | | | |
|---|---|---|---|
| 2012/0120055 A1* | 5/2012 | Seong | H04N 13/128 345/419 |
| 2014/0015937 A1 | 1/2014 | Adachi | |
| 2014/0104382 A1* | 4/2014 | Mori | H04N 13/341 348/43 |

FOREIGN PATENT DOCUMENTS

| | | |
|---|---|---|
| JP | 2010-057619 A | 3/2010 |
| JP | 2012-205148 A | 10/2012 |
| WO | 2012/046369 A1 | 4/2012 |
| WO | 2012/133117 A1 | 10/2012 |

* cited by examiner

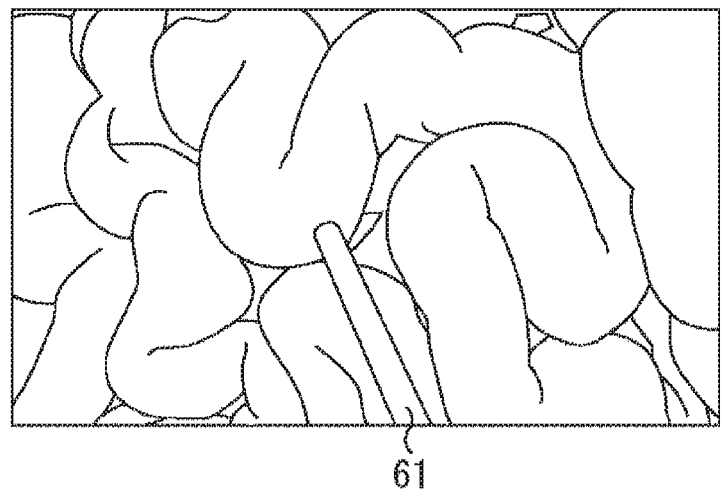
FIG. 16A  OBJECT IMAGE
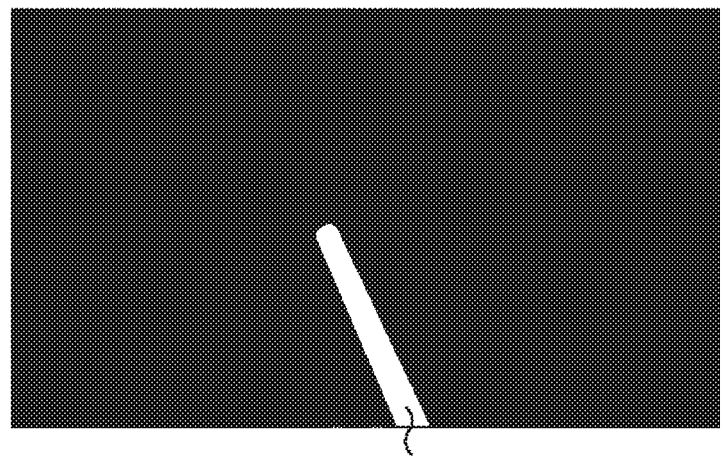
FIG. 16B  FORCEPS REGION IMAGE

IMAGE PROCESSING DEVICE, IMAGE PROCESSING METHOD, AND ENDOSCOPE SYSTEM

CROSS REFERENCE TO RELATED APPLICATIONS

This application is a U.S. National Phase of International Patent Application No. PCT/JP2016/050016 filed on Jan. 4, 2016, which claims priority benefit of Japanese Patent Application No. JP 2015-004127 filed in the Japan Patent Office on Jan. 13, 2015. Each of the above-referenced applications is hereby incorporated herein by reference in its entirety.

TECHNICAL FIELD

The present technology relates to image processing devices, image processing methods, programs, and endoscope systems, and more particularly, to an image processing device, an image processing method, a program, and an endoscope system that reduce a burden on a user, for example.

BACKGROUND ART

To smoothly guide a procedure tool in the depth direction in a procedure such as a medical operation or diagnosis using an endoscope, for example, an endoscope system is required to capture a three-dimensional (3D) image of (the inside of) a human body and display the resultant 3D endoscopic image (see Patent Document 1, for example).

CITATION LIST

Patent Document

Patent Document 1: JP 3869029 B1

SUMMARY OF THE INVENTION

Problems to be Solved by the Invention

With a 3D endoscopic image, a user can obtain depth-direction information by viewing the 3D endoscopic image, and thus, guide a procedure tool smoothly in the depth direction, for example.

Meanwhile, the 3D endoscopic image is formed with a left-eye image to be viewed with the left eye of the user and a right-eye image to be viewed with the right eye of the user, for example. In addition, there is a parallax between the left-eye image and the right-eye image constituting the 3D endoscopic image, and, by virtue of the parallax, the user viewing the 3D endoscopic image perceives the depth-direction information.

In the above manner, a user viewing a 3D endoscopic image can perceive depth-direction information by virtue of the parallax of the 3D endoscopic image. However, in viewing such a 3D endoscopic image, a user might feel strangeness or discomfort specific to 3D images, and such strangeness or discomfort puts a burden on the user in some cases.

That is, in a case where an object with active movement is appearing in a 3D endoscopic image, or where an object extending in the depth direction from the front side moves on the front side, for example, the user viewing the 3D endoscopic image might feel burdened.

The present technology has been developed in view of those circumstances, and is to reduce the burden on a user.

Solutions to Problems

An image processing device or a program of the present technology is an image processing device including a parallax amount adjustment unit that adjusts the parallax amount of a three-dimensional (3D) biological image of an imaged living organism, depending on whether the parallax of the 3D biological image puts a burden on a user, or a program for causing a computer to function as such an image processing device.

An image processing method of the present technology is an image processing method including the step of adjusting the parallax amount of a three-dimensional (3D) biological image of an imaged living organism, depending on whether the parallax of the 3D biological image puts a burden on a user.

An endoscope system of the present technology is an endoscope system including: an endoscope that captures a three-dimensional (3D) image; a parallax amount adjustment unit that adjusts the parallax amount of a 3D biological image, depending on whether the parallax of the 3D biological image puts a burden on a user, the 3D biological image being obtained with the endoscope imaging a living organism; and a display unit that displays the 3D biological image having the parallax amount adjusted by the parallax amount adjustment unit.

In an image processing device, an image processing method, a program, and an endoscope system of the present technology, the parallax amount of a three-dimensional (3D) biological image of an imaged living organism is adjusted, depending on whether the parallax of the 3D biological image puts a burden on a user.

It should be noted that the image processing device may be an independent device, or may be an internal block in a single device.

In addition, the program to be provided may be transmitted via a transmission medium or may be recorded on a recording medium.

Effects of the Invention

According to the present technology, it is possible to reduce a burden on a user.

It should be noted that effects of the present technology are not limited to the effect described herein, and may include any of the effects described in the present disclosure.

BRIEF DESCRIPTION OF DRAWINGS

FIGS. 16A and 16B are views of an example forceps region image generated by a forceps region detection unit 71.

MODE FOR CARRYING OUT THE INVENTION

First Embodiment of an Endoscope System

Figure 1:
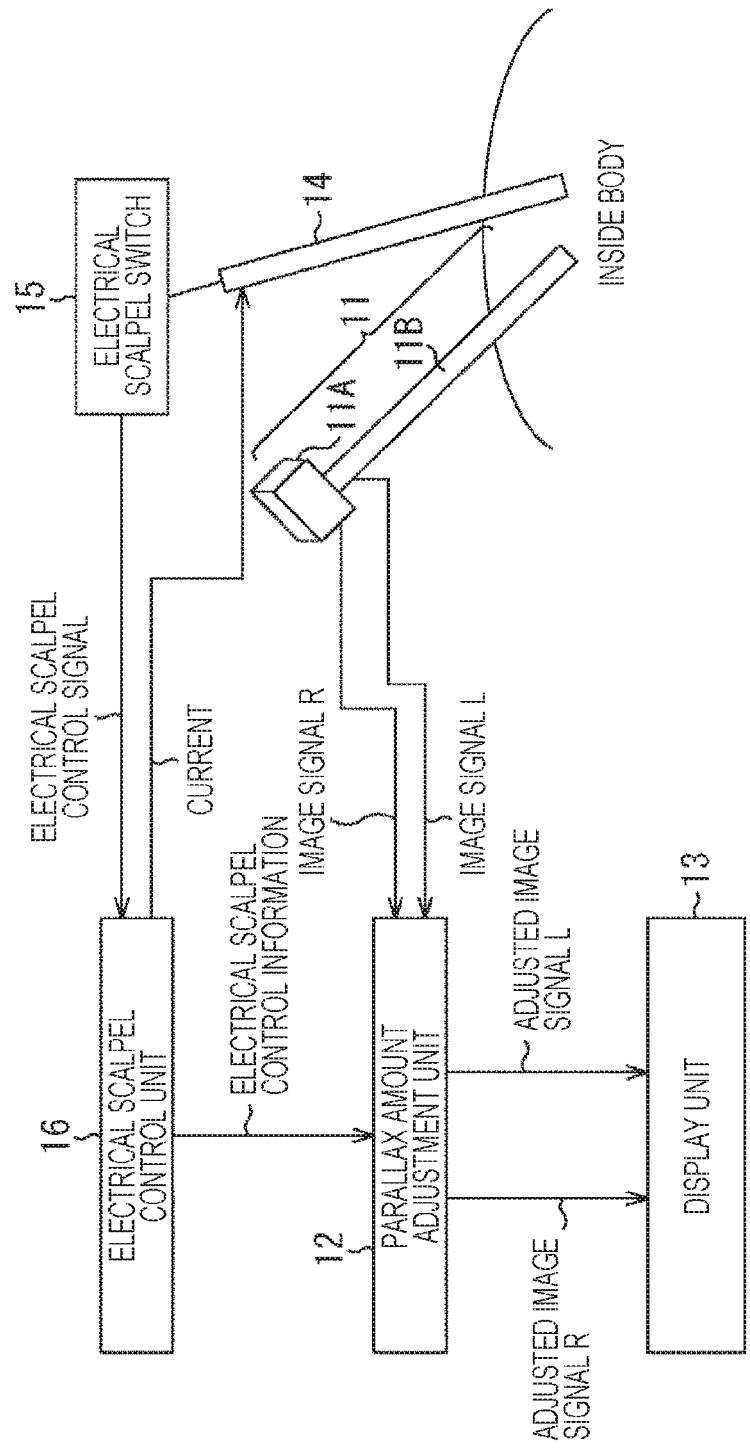
FIG. 1 is a block diagram showing an example configuration of a first embodiment of an endoscope system to which the present technology is applied.

FIG. 1 is a block diagram showing an example configuration of a first embodiment of an endoscope system to which the present technology is applied.

In FIG. 1, the endoscope system includes an endoscope 11, a parallax amount adjustment unit 12, a display unit 13, an electrical scalpel 14, an electrical scalpel switch 15, and an electrical scalpel control unit 16.

The endoscope 11 is inserted into a body cavity of a patient (a human body), for example, and captures an endoscopic image that is a 3D image of the tissues in the body cavity as the object.

That is, in appearance, the endoscope 11 includes a camera head 11A to be held with a hand of an operator (a medical doctor) conducting a medical operation as a user of the endoscope system, and an endoscopic scope 11B to be inserted into the body of a patient.

In an endoscopic operation, or in a medical operation using the endoscope system, the endoscopic scope 11B is inserted into the body, and the user handles the endoscope 11 while holding the camera head 11A.

In the endoscope 11, light is emitted from the tip of the endoscopic scope 11B, for example, and the target site (tissues) as the object in the body of the patient is illuminated with the light. The light illuminating the object is reflected by the object, and the reflected light from the object enters from the tip of the endoscopic scope 11B. In the endoscope 11, the light entering from the tip of the endoscopic scope 11B is then received, and is photoelectrically converted. As a result, a 3D endoscopic image of the object is captured.

Here, the 3D endoscopic image captured by the endoscope 11 is formed with an image signal L of a left-eye image to be viewed with the left eye, and an image signal R of a right-eye image to be viewed with the right eye. There is a parallax between the right-eye image and the right-eye image, and the user can perceive information in the depth direction by viewing the left-eye image and the right-eye image having the parallax with the left eye and the right eye, respectively.

The image signal L of the left-eye image and the image signal R of the right-eye image, which constitute the 3D endoscopic image captured by the endoscope 11, are supplied to the parallax amount adjustment unit 12.

Depending on whether the parallax (between the image signals L and R) of the 3D endoscopic image from the endoscopic image 11 is going to put a burden on the user to view the endoscopic image, the parallax amount adjustment unit 12 adjusts the parallax amount of the 3D endoscopic image from the endoscopic image 11 so as to reduce the burden on the user.

Specifically, in FIG. 1, the parallax amount adjustment unit 12 detects (determines) whether the parallax of the 3D endoscopic image from the endoscopic image 11 is going to put a burden on the user, in accordance with electrical scalpel control information supplied from the electrical scalpel control unit 16, as described later. Then, in a case where the parallax of the 3D endoscopic image from the endoscopic image 11 is going to put a burden on the user, the parallax amount adjustment unit 12 adjusts the parallax amount of the 3D endoscopic image from the endoscopic image 11 so that the parallax becomes smaller.

The parallax amount adjustment unit 12 supplies the display unit 13 with the image signal L (hereinafter also referred to as the adjusted image signal L) of the left-eye image and the image signal R (hereinafter also referred to as the adjusted image signal R) of the right-eye image, which constitute the 3D endoscopic image having its parallax amount adjusted.

The display unit 13 is a display device such as a head mount display that can display a 3D image, and displays the 3D endoscopic image supplied from the parallax amount adjustment unit 12.

Note that the (adjusted) image signal L of the left-eye image and the (adjusted) image signal R of the right-eye image, which constitute the 3D endoscopic image, are displayed by a side-by-side method, a line-by-line method, or a frame sequential method, for example. The display method for displaying a 3D image on the display unit 13 is not limited to any particular method.

The electrical scalpel 14 is a procedure tool that can carry out a procedure to cut tissues of a human body by applying a high-frequency current supplied from the electrical scalpel control unit 16 to the human body.

In this specification, the tools to be used to conduct a procedure in a medical operation or diagnosis using the endoscope system are called procedure tools, and, among the procedure tools, the tools to be used in a medical operation are called medical operation tools. The electrical scalpel 14 is one of the medical operation tools called energy devices. The energy devices include not only devices using electrical current like the electrical scalpel 14, but also devices using ultrasound waves, for example.

The electrical scalpel switch 15 is operated by the user, for example, when the electrical current to be applied to the electrical scalpel 14 is switch on or off. Operated to switch on or off the application of the electrical current, the electrical scalpel switch 15 supplies electrical scalpel control unit 16 with an electrical scalpel control signal corresponding to the operation.

In accordance with the electrical scalpel control signal supplied from the electrical scalpel switch 15, the electrical scalpel control unit 16 switches on or off the supply of the high-frequency current to the electrical scalpel 14. In accordance with the electrical scalpel control signal, the electrical scalpel control unit 16 also supplies the parallax amount adjustment unit 12 with electrical scalpel control information indicating that the electrical scalpel 14 is on or off.

In the endoscope system having the above configuration, the user (operator) inserts the endoscopic scope 11B into the body of a patient, and the endoscope 11 captures a 3D endoscopic image of the target site (tissues) to be the object in the body of the patient.

The 3D endoscopic image (the image signal L of the left-eye image and the image signal R of the right-eye image constituting the 3D endoscopic image) captured by the endoscope 11 is supplied from the endoscope 11 to the parallax amount adjustment unit 12, and is further supplied from the parallax amount adjustment unit 12 to the display unit 13, which then displays the 3D endoscopic image.

When the user switches on the electrical scalpel switch 15 to conduct a medical operation while looking at the 3D endoscopic image displayed on the display unit 13, an electrical scalpel control signal indicating "on" is supplied to the electrical scalpel control unit 16.

In accordance with the "on" electrical scalpel control signal supplied from the electrical scalpel switch 15, the electrical scalpel control unit 16 switches on (starts) the supply of a high-frequency current to the electrical scalpel 14, so that the user can cut the tissues of the patient with the electrical scalpel 14.

The electrical scalpel control unit 16 also supplies the parallax amount adjustment unit 12 with electrical scalpel control information indicating that the electrical scalpel 14 is on or off.

In a case where the electrical scalpel control information indicates that the electrical scalpel 14 is on, and accordingly, the electrical scalpel 14 is being used, the parallax amount adjustment unit 12 determines that the parallax of the 3D endoscopic image displayed on the display unit 13 is putting a burden on the user, and adjusts the parallax amount of the 3D endoscopic image supplied from the endoscope 11.

Specifically, in a case where the electrical scalpel 14 is being used, when tissues of a human body are cut with the electrical scalpel 14, mist or smoke is generated. If the mist or smoke generated while the electrical scalpel 14 is being used actively moves and appears in the 3D endoscopic image by approaching the tip of the endoscopic scope 11B, the user viewing the 3D endoscopic image might feel discomfort from the mist or smoke with the active movement.

The user's discomfort caused by the actively moving mist or smoke appearing in the 3D endoscopic image increases the burden on the user viewing the 3D endoscopic image, and prevents the user from paying close attention to the originally intended site.

Therefore, in a case where the electrical scalpel 14 is being used, the parallax amount adjustment unit 12 adjusts the parallax amount of the 3D endoscopic image supplied from the endoscope 11 to reduce the parallax, so that the burden on the user due to the mist or smoke appearing in the 3D endoscopic image while the electrical scalpel 14 is being used is reduced.

The display unit 13 then displays the 3D endoscopic image having its parallax amount adjusted by the parallax amount adjustment unit 12.

Note that, although the electrical scalpel 14 is used as the energy device in FIG. 1, an energy device other than the electrical scalpel 14, such as a device that uses ultrasound waves, can be used as the energy device.

Figure 2:
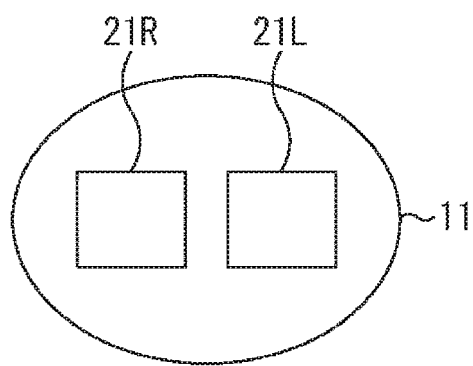
FIG. 2 is a diagram schematically showing an example configuration of an endoscope 11 that captures a 3D endoscopic image.

FIG. 2 is a diagram schematically showing an example configuration of the endoscope 11 that captures the 3D endoscopic image.

The endoscope 11 includes two imaging elements (image sensors) 21L and 21R.

The imaging element 21L captures an image to be the left-eye image. The imaging element 21R captures an image to be the right-eye image.

In FIG. 2, the imaging elements 21L and 21R are aligned in a horizontal direction (a lateral direction), so that the imaging elements 21L and 21R capture the left-eye image and the right-eye image, respectively, with a parallax existing in between.

It should be noted that, in the endoscope 11, the imaging elements 21L and 21R can be disposed at the tip of the endoscopic scope 11B or in the camera head 11A, for example.

Meanwhile, a method of capturing a 3D image may be a method of capturing an image with two lenses or a method of capturing an image with one lens (a single lens), for example. However, the method of capturing a 3D endoscopic image in the endoscope 11 is not limited to any particular method.

Figure 3:
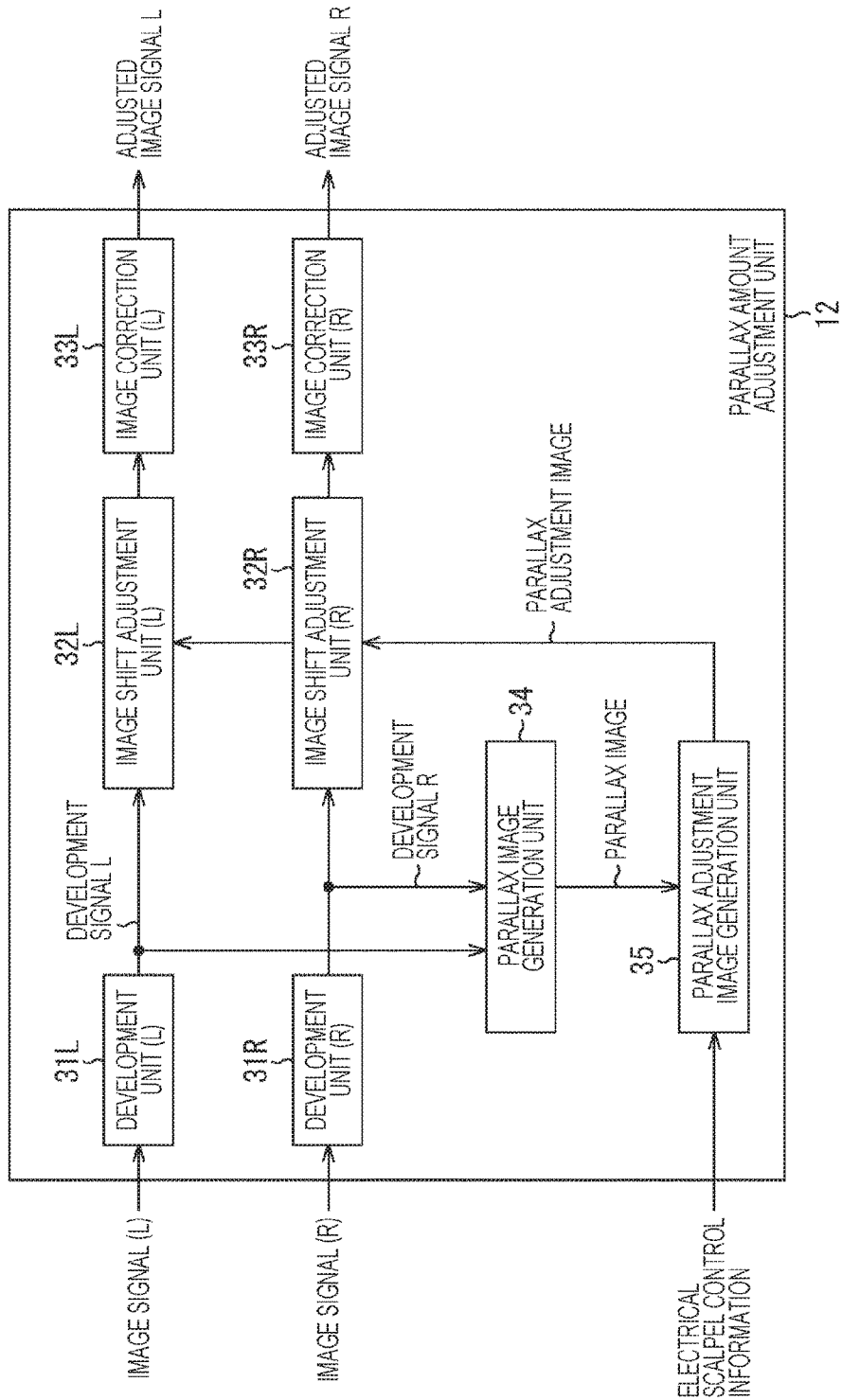
FIG. 3 is a block diagram showing an example configuration of a parallax amount adjustment unit 12.

FIG. 3 is a block diagram showing an example configuration of the parallax amount adjustment unit 12 shown in FIG. 1.

In FIG. 3, the parallax amount adjustment unit 12 includes development units 31L and 31R, image shift adjustment units 32L and 32R, image correction units 33L and 33R, a parallax image generation unit 34, and a parallax adjustment image generation unit 35.

The image signal L of the left-eye image forming a 3D endoscopic image is supplied from the endoscope 11 to the development unit 31L.

Here, the left-eye image and the right-eye image constituting the 3D endoscopic image captured by the endoscope 11 are so-called RAW images in a predetermined pattern such as a Bayer pattern.

The development unit 31L performs a development process on the image signal L of the left-eye image supplied from the endoscope 11, to generate a development signal L including image signals of the respective planes of red (R), green (G), and blue (B). The development unit 31L supplies the development signal L to the image shift adjustment unit 32L and the parallax image generation unit 34.

Not only the development signal L of the left-eye image from the development unit 31L, but also a parallax adjustment image that will be described later is supplied from the parallax adjustment image generation unit 35 to the image shift adjustment unit 32L.

In accordance with the parallax adjustment image supplied from the parallax adjustment image generation unit 35, the image shift adjustment unit 32L horizontally shifts the pixel values of the pixels of (the development signal L of) the left-eye image from the development unit 31L, to adjust the parallax amount of the 3D endoscopic image formed with the left-eye image from the development unit 31L.

The image shift adjustment unit 32L supplies the image correction unit 33L with (the image signal of) the left-eye image having its pixel values shifted.

The image correction unit 33L corrects the left-eye image by interpolating missing pixels among the pixels constituting the left-eye image that has its pixel values shifted and been supplied from the image shift adjustment unit 32L.

Here, missing pixels with no pixel values might exist among the pixels constituting the left-eye image that has its pixel values shifted and been supplied from the image shift adjustment unit 32L to the image correction unit 33L.

That is, missing pixels with no pixel values might exist in the left-eye image having its pixel values shifted, due to false detection of a parallax amount at the parallax image generation unit 34 described later, overlapping of shift destinations in the shifting of the pixel values at the image shift adjustment unit 32L, existence of pixels not serving as shift destinations, or the like (the same applies to the right-eye image).

The image correction unit 33L corrects the left-eye image by interpolating the pixel values of the missing pixels in the left-eye image, using the pixel values of pixels that are located near the missing pixels but are not missing pixels. The image correction unit 33L then supplies the display unit 13 with the image signal of the corrected left-eye image, or an adjusted image signal L that is the image signal of the left-eye image that has no missing pixels and forms the 3D endoscopic image having its parallax amount adjusted.

The image signal R of the right-eye image forming the 3D endoscopic image is supplied from the endoscope 11 to the development unit 31R.

The development unit 31R, the image shift adjustment unit 32R, and the image correction unit 33R perform processes similar to the processes to be performed by the development unit 31L, the image shift adjustment unit 32L, and the image correction unit 33L, respectively.

Specifically, the development unit 31R performs a development process on the image signal R of the right-eye image supplied from the endoscope 11, to generate a development signal R including image signals of the respective planes of R, G, and B. The development unit 31R supplies the development signal R to the image shift adjustment unit 32R and the parallax image generation unit 34.

In accordance with the parallax adjustment image supplied from the parallax adjustment image generation unit 35, the image shift adjustment unit 32R horizontally shifts the pixel values of the pixels of (the development signal R of) the right-eye image from the development unit 31R, to adjust the parallax amount of the 3D endoscopic image formed with the right-eye image from the development unit 31R.

The image shift adjustment unit 32R supplies the image correction unit 33R with (the image signal of) the right-eye image having its pixel values shifted.

Like the pixel value correction unit 33L, the image correction unit 33R corrects the right-eye image by interpolating missing pixels among the pixels constituting the right-eye image that has its pixel values shifted and been supplied from the image shift adjustment unit 32R. The image correction unit 33R then supplies the display unit 13 with an adjusted image signal R that is the image signal of the left-eye image that is obtained as a result of the correction on the right-eye image, has no missing pixels, and forms the 3D endoscopic image having its parallax amount adjusted.

Using (the development signal L of) the left-eye image supplied from the development unit 31L and (the development signal R of) the right-eye image supplied from the development unit 31R, the parallax image generation unit 34 detects a parallax amount between the left-eye image and the right-eye image.

That is, with reference to either the left-eye image from the development unit 31L or the right-eye image from the development unit 31R, or with reference to the left-eye image, for example, the parallax image generation unit 34 detects corresponding pixels in the right-eye image, the corresponding pixels corresponding to the respective pixels in the left-eye image.

Specifically, the parallax image generation unit 34 sequentially selects each pixel in the left-eye image as a target pixel, and detects the corresponding pixel corresponding to the target pixel from among the pixels in the right-eye image.

The corresponding pixel can be detected by block matching in which a block similar to the block including the target pixel is searched in the horizontal direction in the right-eye image, for example.

The parallax image generation unit 34 detects a distance from the position corresponding to the target pixel to the position of the corresponding pixel as the parallax amount between the target pixel and the corresponding pixel in the right-eye image, and generates a parallax image having the parallax amount as a pixel value.

That is, the parallax image generation unit 34 generates a parallax image that is an image having the parallax amount detected in regard to the target pixel as the pixel value of the pixel located in the position of the target pixel.

After generating the parallax image, the parallax image generation unit 34 supplies the parallax image to the parallax adjustment image generation unit 35.

Using the parallax image supplied from the parallax image generation unit 34, the parallax adjustment image generation unit 35 generates a parallax adjustment image having a pixel value that is the parallax adjustment value for adjusting the parallax amount serving as a pixel value of the parallax image.

That is, not only the parallax image from the parallax image generation unit 34, but also electrical scalpel control information from the electrical scalpel control unit 16 is supplied to the parallax amount adjustment image generation unit 35.

In accordance with the electrical scalpel control information, the parallax amount adjustment image generation unit 35 generates a parallax adjustment image, using the parallax image supplied from the parallax image generation unit 34.

Specifically, the parallax amount that is the pixel value of the pixel in a position (x, y) in the parallax image is expressed as d(x, y), and the parallax adjustment value that is the pixel value of the pixel in the position (x, y) in the parallax adjustment image is expressed as c(x, y).

The parallax adjustment image generation unit 35 determines the parallax adjustment value c(x, y) for adjusting the parallax amount d(x, y), according to an expression (1) or an expression (2), for example.

$$c(x,y)=(d(x,y)-d(x,y)/a)/2 \qquad (1)$$

$$c(x,y)=0 \qquad (2)$$

It should be noted that, in the expression (1), "a" is a constant equal to or greater than 1, and the value thereof is experimentally determined by the developer of the endoscope system, for example.

Meanwhile, which one of the expressions (1) and (2) is to be used in determining the parallax adjustment value c(x, y) is controlled in accordance with the electrical scalpel control information.

Specifically, in a case where the electrical scalpel control information indicates that the electrical scalpel 14 is on, the parallax adjustment value c(x, y) is determined according to the expression (1). In addition, in a case where the electrical scalpel control information indicates that the electrical scalpel 14 is off, on the other hand, the parallax adjustment value c(x, y) is determined according to the expression (2).

Here, according to the expression (1), the parallax adjustment value c(x, y) is determined to be a value ((d(x, y)−d(x, y)/a)/2) corresponding to the parallax amount d(x, y). On the other hand, according to the expression (2), the parallax adjustment value c(x, y) is determined to be 0.

Accordingly, in a case where the electrical scalpel 14 is on, and mist or smoke is easily generated by usage of the electrical scalpel 14, the parallax adjustment value c(x, y) corresponding to the parallax amount d(x, y) is determined according to the expression (1).

In addition, in a case where the electrical scalpel 14 is off, and mist or smoke is not generated by usage of the electrical scalpel 14, the parallax adjustment value c(x, y) is determined to be 0 according to the expression (2).

The parallax adjustment image generation unit 35 generates a parallax adjustment image having the above parallax adjustment value c(x, y) as a pixel value, and supplies the parallax adjustment image to the image shift adjustment units 32L and 32R.

In accordance with the parallax adjustment image supplied from the parallax adjustment image generation unit 35 as above, the image shift adjustment units 32L and 32R horizontally shift the pixel values of the pixels in the left-eye image and the right-eye image, to adjust the parallax amount of the 3D endoscopic image formed with the left-eye image and the right-eye image.

Figure 4:
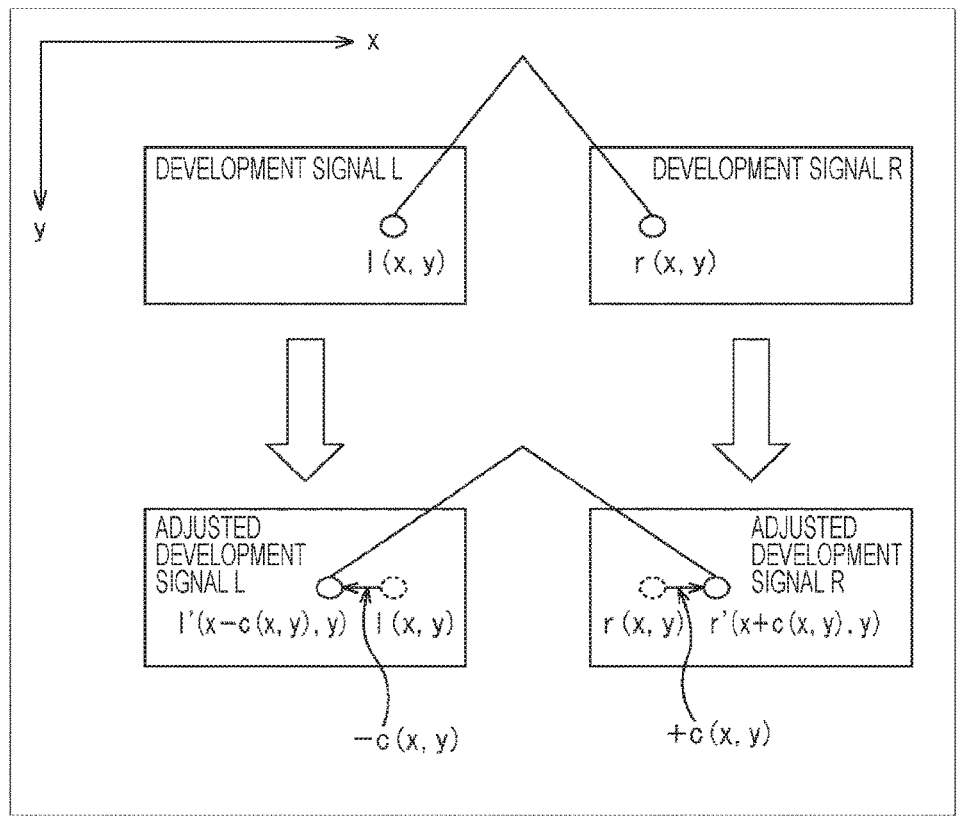
FIG. 4 is a diagram for explaining adjustment of a parallax amount through shifting of pixel values at image shift adjustment units 32L and 32R.

FIG. 4 is a diagram for explaining adjustment of a parallax amount through shifting of pixel values at the image shift adjustment units 32L and 32R.

Here, the pixel in a position (x, y) in the development signal L of the left-eye image is the target pixel, and the pixel value of the target pixel is expressed as l(x, y). Also, the pixel value of the corresponding pixel corresponding to the target pixel in the development signal R of the right-eye image is expressed as r(x, y).

In accordance with the parallax adjustment value c(x, y) that is the pixel value of the pixel in the position (x, y) in the parallax adjustment image, the image shift adjustment unit 32L horizontally shifts the pixel value l(x, y) of the target pixel in the development signal L of the left-eye image, to adjust the parallax amount between the target pixel and the corresponding pixel.

Specifically, according to an expression (3), for example, the image shift adjustment unit 32L obtains a pixel value l'(x−c(x, y), y) in the position determined by horizontally shifting the pixel value l(x, y) of the target pixel by −c(x, y).

$$l'(x-c(x,y),y)=l(x,y) \quad (3)$$

Likewise, in accordance with the parallax adjustment value c(x, y) that is the pixel value of the pixel in the position (x, y) in the parallax adjustment image, the image shift adjustment unit 32R horizontally shifts the pixel value r(x, y) of the corresponding pixel in the development signal R of the right-eye image, to adjust the parallax amount between the target pixel and the corresponding pixel.

Specifically, according to an expression (4), for example, the image shift adjustment unit 32R obtains a pixel value r'(x+c(x, y), y) in the position determined by horizontally shifting the pixel value r(x, y) of the corresponding pixel by +c(x, y).

$$r'(x+c(x,y),y)=r(x,y) \quad (4)$$

In a case where the parallax adjustment value c(x, y) is greater than 0, the parallax between the pixel values l'(x−c(x, y), y) and r'(x+c(x, y), y) after the shifting is smaller than the parallax between the pixel values l(x, y) and r(x, y) prior to the shifting. Thus, the burden to be felt by the user due to the parallax can be reduced.

At the image shift adjustment units 32L and 32R, each pixel in the development signal L of the left-eye image is sequentially selected as the target pixel, and the pixel values of the respective pixels in the development signal L of the left-eye image and the development signal R of the right-eye image are shifted.

The image shift adjustment unit 32L then supplies the image correction unit 33L with an adjusted development signal L of the left-eye image, the adjusted development signal L being the signal of the image obtained by shifting the pixel values of the respective pixels in the development signal L of the left-eye image. Likewise, the image shift adjustment unit 32R supplies the image correction unit 33R with an adjusted development signal R of the right-eye image, the adjusted development signal R being the signal of the image obtained by shifting the pixel values of the respective pixels in the development signal R of the right-eye image.

As described above with reference to FIG. 3, if the electrical scalpel 14 is off at this stage, the parallax adjustment value c(x, y) is 0 according to the expression (2), and therefore, no substantial adjustment is performed on the parallax amount by the image shift adjustment units 32L and 32R shifting the pixel values.

If the electrical scalpel 14 is on, on the other hand, the parallax adjustment value c(x, y) is determined according to the expression (1), and the image shift adjustment units 32L and 32R shift the pixel values in accordance with the parallax adjustment value c(x, y), to adjust the parallax amount and reduce the parallax.

When the electrical scalpel 14 in an on-state is brought into contact with tissues of a human body (the subject (the patient)), mist or smoke is generated. If the mist or smoke actively moves and appears in the 3D endoscopic image by approaching the tip of the endoscopic scope 11B, the user viewing the 3D endoscopic image might feel 3D-image-specific discomfort from the mist or smoke with the active movement.

The user's discomfort caused by the actively moving mist or smoke appearing in the 3D endoscopic image increases the burden on the user viewing the 3D endoscopic image, and prevents the user from paying close attention to the originally intended site.

In the endoscope system in FIG. 1, in a case where the electrical scalpel 14 is on, the parallax amount of a 3D endoscopic image is adjusted so that the parallax becomes smaller, as described above. Thus, the burden on the user viewing the 3D endoscopic image can be reduced.

Figure 5:
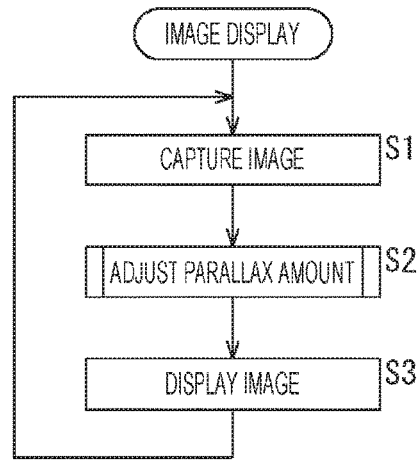
FIG. 5 is a flowchart for explaining an example of an image display process to display a 3D endoscopic image.

FIG. 5 is a flowchart for explaining an example of an image display process to display a 3D endoscopic image in the endoscope system in FIG. 1.

In step S1, the endoscope 11 is inserted into a body cavity of a patient (a human body), for example, and captures a 3D endoscopic image of the object that is the tissues in the body cavity. The endoscope 11 supplies the parallax amount adjustment unit 12 with the image signal L of the left-eye image and the image signal R of the right-eye image, which constitute the 3D endoscopic image.

The process then advances from step S1 to step S2. The parallax amount adjustment unit 12 adjusts the parallax amount of (the image signals L and R of) the 3D endoscopic image supplied from the endoscopic image 11, and supplies the display unit 13 with (the adjusted image signals L and R of) the 3D endoscopic image having its parallax amount adjusted.

That is, in a case where the parallax of the 3D endoscopic image from the endoscopic image 11 is going to put a burden on the user viewing the endoscopic image, the parallax amount adjustment unit 12 adjusts the parallax amount of the 3D endoscopic image so that the parallax becomes smaller. The parallax amount adjustment unit 12 then supplies the display unit 13 with the 3D endoscopic image having its parallax amount adjusted, and the process advances from step S2 to step S3.

In step S3, the display unit 13 displays the 3D endoscopic image supplied from the parallax amount adjustment unit 12. After that, the process returns from step S3 to step S1, and a process similar to the above is repeated.

Figure 6:
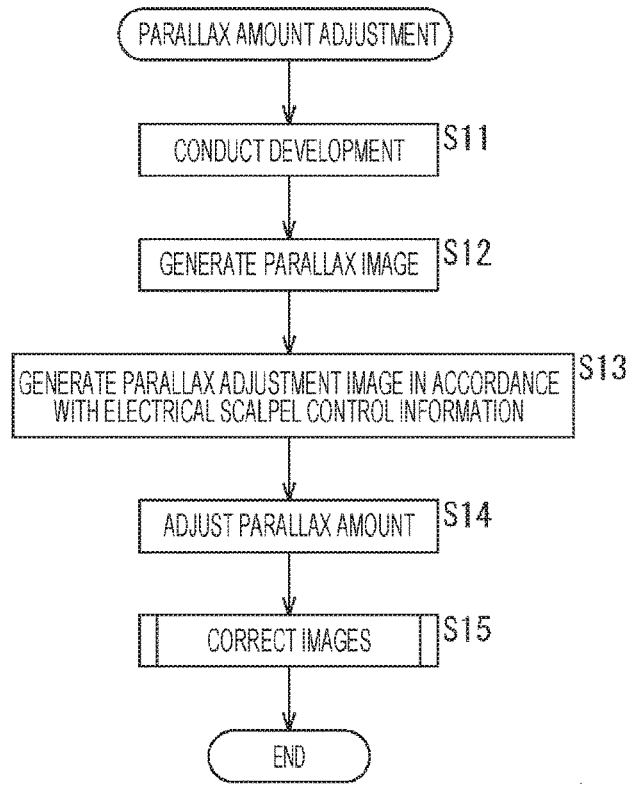
FIG. 6 is a flowchart for explaining an example of a process of adjusting the parallax amount of a 3D endoscopic image.

FIG. 6 is a flowchart for explaining an example of the process to be performed in step S2 in FIG. 5 to adjust the parallax amount of a 3D endoscopic image in the endoscope system shown in FIG. 1.

In step S11, the development units 31L and 31R perform a development process, and the process moves on to step S12.

Specifically, the development unit 31L performs a development process on the image signal L of the left-eye image forming the 3D endoscopic image supplied from the endoscope 11, to generate a development signal L. The development unit 31L supplies the development signal L to the image shift adjustment unit 32L and the parallax image generation unit 34.

The development unit 31R performs a development process on the image signal R of the right-eye image forming the 3D endoscopic image supplied from the endoscope 11, to generate a development signal R. The development unit 31R supplies the development signal R to the image shift adjustment unit 32R and the parallax image generation unit 34.

In step S12, using the left-eye image from the development unit 31L and the right-eye image from the development unit 31R, the parallax image generation unit 34 generates a parallax image having a parallax amount d(x, y) as a pixel value, and supplies the parallax image to the parallax adjustment image generation unit 35. The process then moves on to step S13.

In step S13, in accordance with electrical scalpel control information supplied from the electrical scalpel control unit 16, the parallax adjustment image generation unit 35 generates a parallax adjustment image having the parallax adjustment value c(x, y) as a pixel value, using the parallax image supplied from the parallax image generation unit 34.

The parallax adjustment image generation unit 35 then supplies the parallax adjustment image to the image shift adjustment units 32L and 32R, and the process moves on to step S14.

In step S14, in accordance with the parallax adjustment image supplied from the parallax adjustment image generation unit 35, the image shift adjustment units 32L and 32R horizontally shift the pixel values of the respective pixels in the left-eye image from the development unit 31L and the right-eye image from the development unit 31R, to adjust the parallax amount of the 3D endoscopic image formed with the left-eye image and the right-eye image.

The image shift adjustment unit 32L then supplies the image correction unit 33L with (the adjusted image signal L of) the left-eye image having its pixel values shifted. Further, the image shift adjustment unit 32R supplies the image correction unit 33L with (the adjusted image signal R of) the right-eye image having its pixel values shifted, and the process advances from step S14 to step S15.

In step S15, the image correction unit 33L corrects the left-eye image by interpolating missing pixels among the pixels constituting the left-eye image that has its pixel values shifted and been supplied from the image shift adjustment unit 32L. The image correction unit 33L then supplies the display unit 13 with (the adjusted image signal L of) the left-eye image that is obtained through the left-eye image correction and has no missing pixels.

Further, in step S15, the image correction unit 33R corrects the right-eye image by interpolating missing pixels among the pixels constituting the right-eye image that has its pixel values shifted and been supplied from the image shift adjustment unit 32R. The image correction unit 33R then supplies the display unit 13 with (the adjusted image signal R of) the right-eye image that is obtained through the right-eye image correction and has no missing pixels, and the process comes to an end (or returns).

Figure 7:
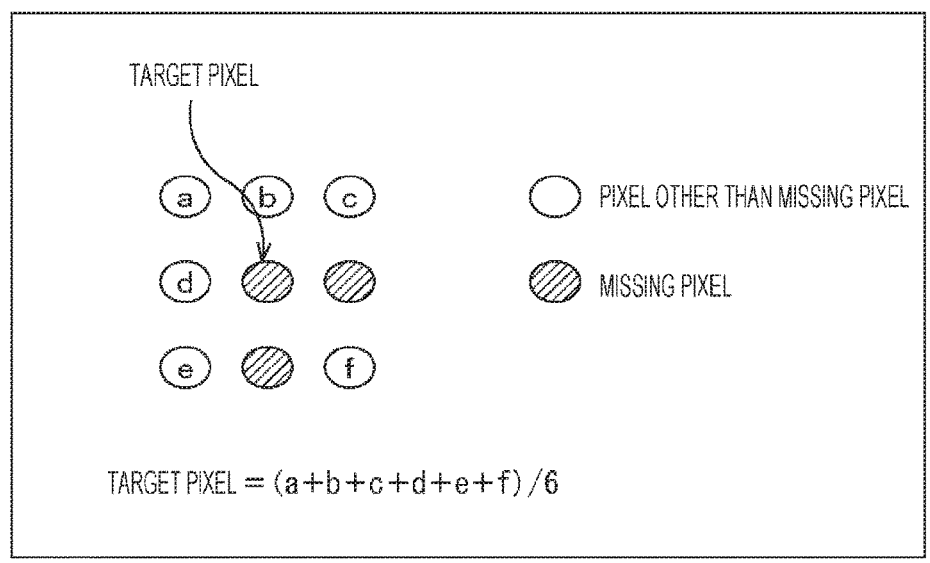
FIG. 7 is a diagram for explaining an example of interpolating of (the pixel values of) missing pixels at image correction units 33L and 33R.

FIG. 7 is a diagram for explaining an example of interpolating of (the pixel values of) missing pixels at the image correction units 33L and 33R.

The image correction unit 33L sequentially selects each of the pixels constituting the left-eye image as the target pixel. Then, in a case where the target pixel is a missing pixel having its pixel value missing due to the shifting of the pixel values at the image shift adjustment unit 32L, the pixel value of the target pixel that is a missing pixel is interpolated.

The pixel value of the target pixel that is a missing pixel is interpolated with the use of the pixel value of a pixel that is not a missing pixel among the pixels located near the target pixel.

Specifically, as shown in FIG. 7, the image correction unit 33L calculates the mean value of the pixel values of the pixels that are not missing pixels among the eight pixels adjacent to the target pixel in the left-eye image, and determines the mean value to be the pixel value of the target pixel that is a missing pixel.

In FIG. 7, of the eight pixels adjacent to the target pixel that is a missing pixel, the right adjacent pixel located to the right of the target pixel and the lower adjacent pixel located immediately below the target pixel are missing pixels. In this case, the pixel value of the target pixel that is a missing pixel is interpolated with the mean value (a+b+c+d+e+f)/6 of the pixel values a, b, c, d, e, and f of the six pixels excluding the right adjacent pixel and the lower adjacent pixel among the eight pixels adjacent to the target pixel that is a missing pixel.

Like the image correction unit 33L, the image correction unit 33R also interpolates missing pixels in the right-eye image.

Figure 8:
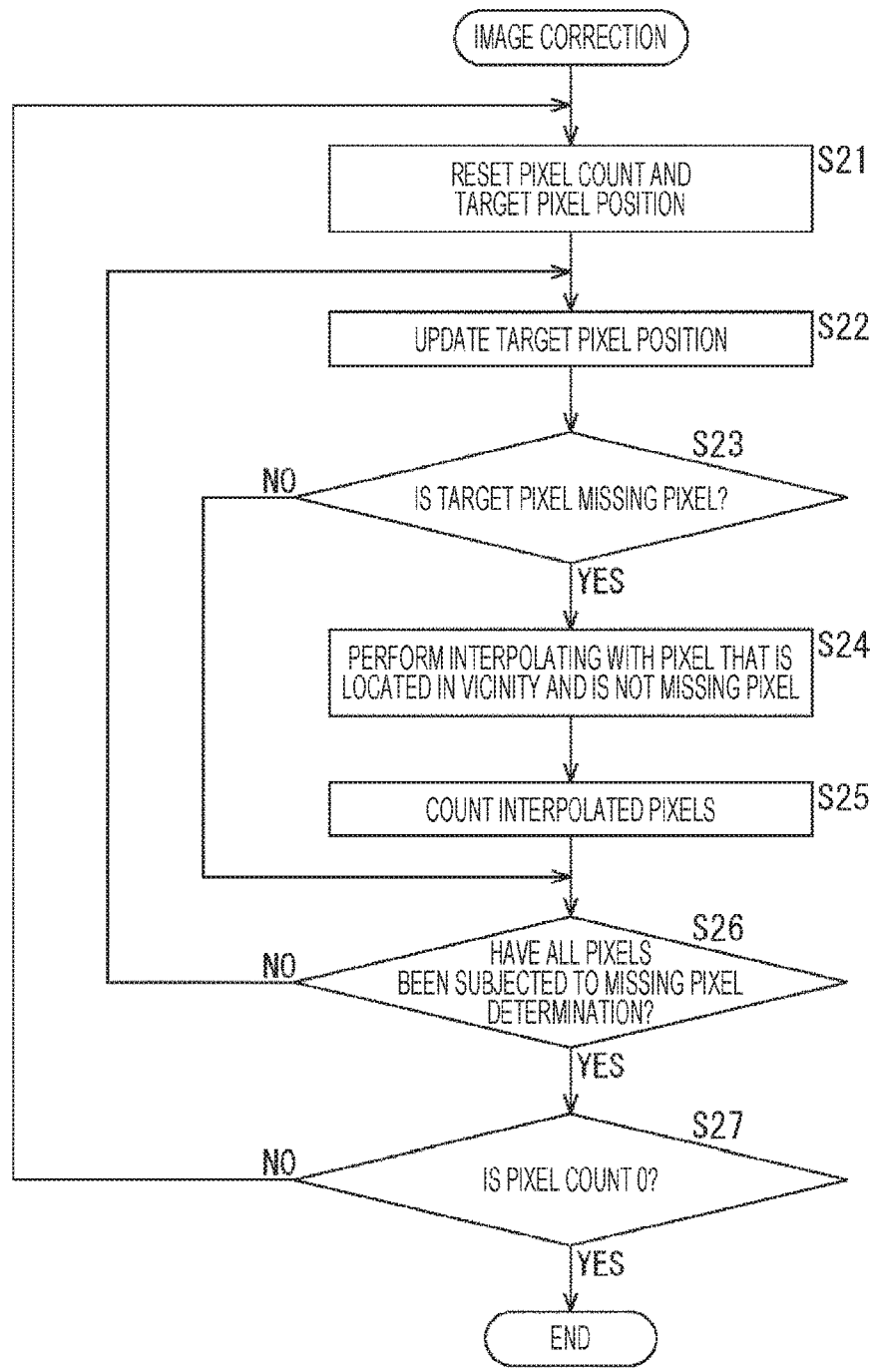
FIG. 8 is a flowchart for explaining an example of a process of correcting a left-eye image and a right-eye image through interpolating of missing pixels.

FIG. 8 is a flowchart for explaining an example of the process to be performed in step S15 in FIG. 6 to correct the left-eye image and the right-eye image through interpolating of missing pixels.

In step S21, the image correction unit 33L resets a pixel count as a variable for counting interpolated pixels (missing pixels), and a target pixel position as a variable representing the position of the pixel serving as the target pixel in the left-eye image. The process then moves on to step S22.

That is, when the pixel count is reset, the pixel count is set at 0, for example. When the target pixel position is reset, the target pixel position is set at the position shifted one pixel from the position of the pixel at the upper left corner of the left-eye image.

In step S22, the image correction unit 33L updates the target pixel position by the amount equivalent to one pixel in a raster scanning order, for example. The process then moves on to step S23.

In step S23, the image correction unit 33L determines whether the pixel in the target pixel position among the pixels in the left-eye image, or the target pixel, is a missing pixel.

If the target pixel is determined not to be a missing pixel in step S23, the process skips steps S24 and S25, and moves on to step S26.

In addition, if the target pixel is determined to be a missing pixel in step S23, on the other hand, the process moves on to step S24.

In step S24, the image correction unit 33L interpolates the pixel value of the target pixel that is a missing pixel, using the pixel value of a pixel that is not a missing pixel among the pixels located near (in the vicinity of) the target pixel among the pixels in the left-eye image. The process then moves on to step S25.

In step S25, the image correction unit 33L increments an interpolated pixel number by 1, the interpolated pixel number being a variable for counting the pixels interpolated in step S24. The process then moves on to step S26.

In step S26, the image correction unit 33L determines whether all the pixels constituting the left-eye image have been selected as the target pixel and been subjected to the determination as to whether the target pixel is a missing pixel.

If it is determined in step S26 that not all the pixels constituting the left-eye image have been selected as the target pixel, the process returns to step S22, and thereafter, a similar process is repeated.

In addition, if it is determined in step S26 that all the pixels constituting the left-eye image have been selected as the target pixel, or if the target pixel position is the position of the last pixel in the raster scanning order of the left-eye image, on the other hand, the process moves on to step S27, and the image correction unit 33L determines whether the pixel count is 0.

If the pixel count is determined not to be 0 in step S27, the process returns to step S21, and thereafter, a similar process is repeated.

Specifically, in a case where a missing pixel existed in the left-eye image, and the pixel value of the missing pixel was interpolated in the last loop process in steps S22 through S26, there still is a possibility of existence of a missing pixel in the left-eye image, and therefore, the process in steps S21 through S27 is recursively repeated.

If the pixel count is determined to be 0 in step S27, on the other hand, the process comes to an end (returns).

Specifically, in a case where nonexistence of missing pixels in the left-eye image was confirmed in the last loop process in steps S22 through S26, the image correction unit 33L supplies the display unit 13 with the left-eye image obtained through the interpolating of pixel values in step S24, and the process then comes to an end.

In this process, the image correction unit 33L can determine whether the target pixel is a missing pixel, using a missing flag indicating a missing pixel, for example.

Specifically, the image shift adjustment unit 32L buries (stores) the missing flag into the memory storing the shifted pixel values, and writes the shifted pixel values into the memory in an overwriting manner.

In this case, the missing flag remains at a memory address at which any shifted pixel value has not been written, and therefore, the pixel corresponding to the memory address at which the missing flag is still stored can be determined to be a missing pixel.

It should be noted that, like the image correction unit 33L, the image correction unit 33R corrects the right-eye image.

Second Embodiment of an Endoscope System

Figure 9:
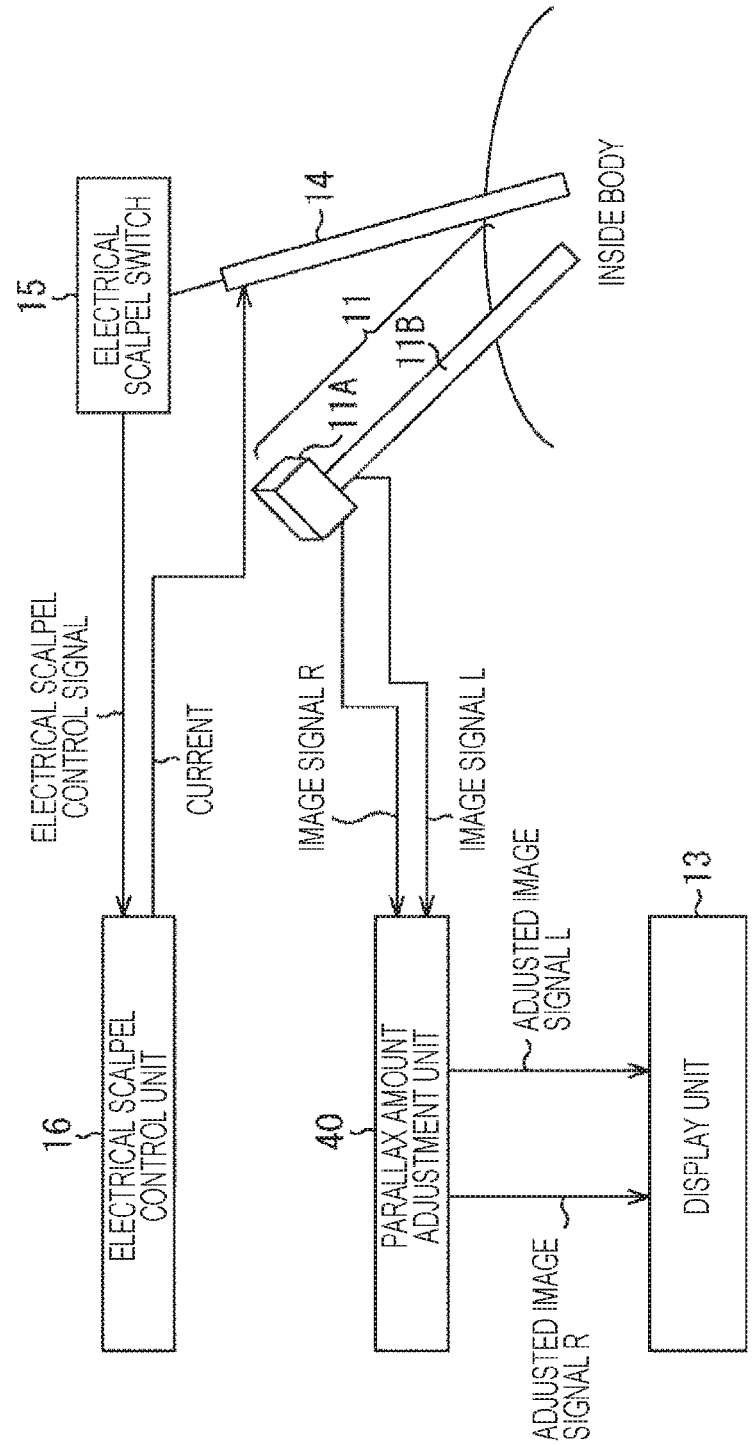
FIG. 9 is a block diagram showing an example configuration of a second embodiment of an endoscope system to which the present technology is applied.

FIG. 9 is a block diagram showing an example configuration of a second embodiment of an endoscope system to which the present technology is applied.

Note that, in the drawing, the components equivalent to those in FIG. 1 are denoted by the same reference numerals as those used in FIG. 1, and explanation thereof will not be repeated below.

In FIG. 9, the endoscope system is the same as that shown in FIG. 1 in including an endoscope 11, a display unit 13, an electrical scalpel 14, an electrical scalpel switch 15, and an electrical scalpel control unit 16.

However, the endoscope system in FIG. 9 differs from that shown in FIG. 1 in that the parallax amount adjustment unit 12 is replaced with a parallax amount adjustment unit 40.

In a case where the parallax of a 3D endoscopic image supplied from the endoscopic image 11 is going to put a burden on the user to view the endoscopic image, the parallax amount adjustment unit 40, like the parallax amount adjustment unit 12 in FIG. 1, adjusts the parallax amount of the 3D endoscopic image so as to reduce the burden on the user, and supplies the adjusted endoscopic image to the display unit 13.

However, unlike the parallax amount adjustment unit 12 that adjusts a parallax amount in accordance with electrical scalpel control information, the parallax amount adjustment unit 40 adjusts the parallax amount of a burdening region where the parallax of a 3D endoscopic image supplied from the endoscopic image 11 becomes a burden, in accordance with the 3D endoscopic image.

Therefore, in the endoscope system in FIG. 9, electrical scalpel control information is not supplied from the electrical scalpel control unit 16 to the parallax amount adjustment unit 40 as in the case illustrated in FIG. 1.

In the endoscope system in FIG. 9, however, electrical scalpel control information may be supplied from the electrical scalpel control unit 16 to the parallax amount adjustment unit 40 as in the case illustrated in FIG. 1. In that case, when the electrical scalpel control information indicates that the electrical scalpel 14 is on, the parallax amount adjustment unit 40 can adjust the parallax amount of the burdening region in a 3D endoscopic image supplied from the endoscopic image 11, in accordance with the 3D endoscopic image.

Figure 10:
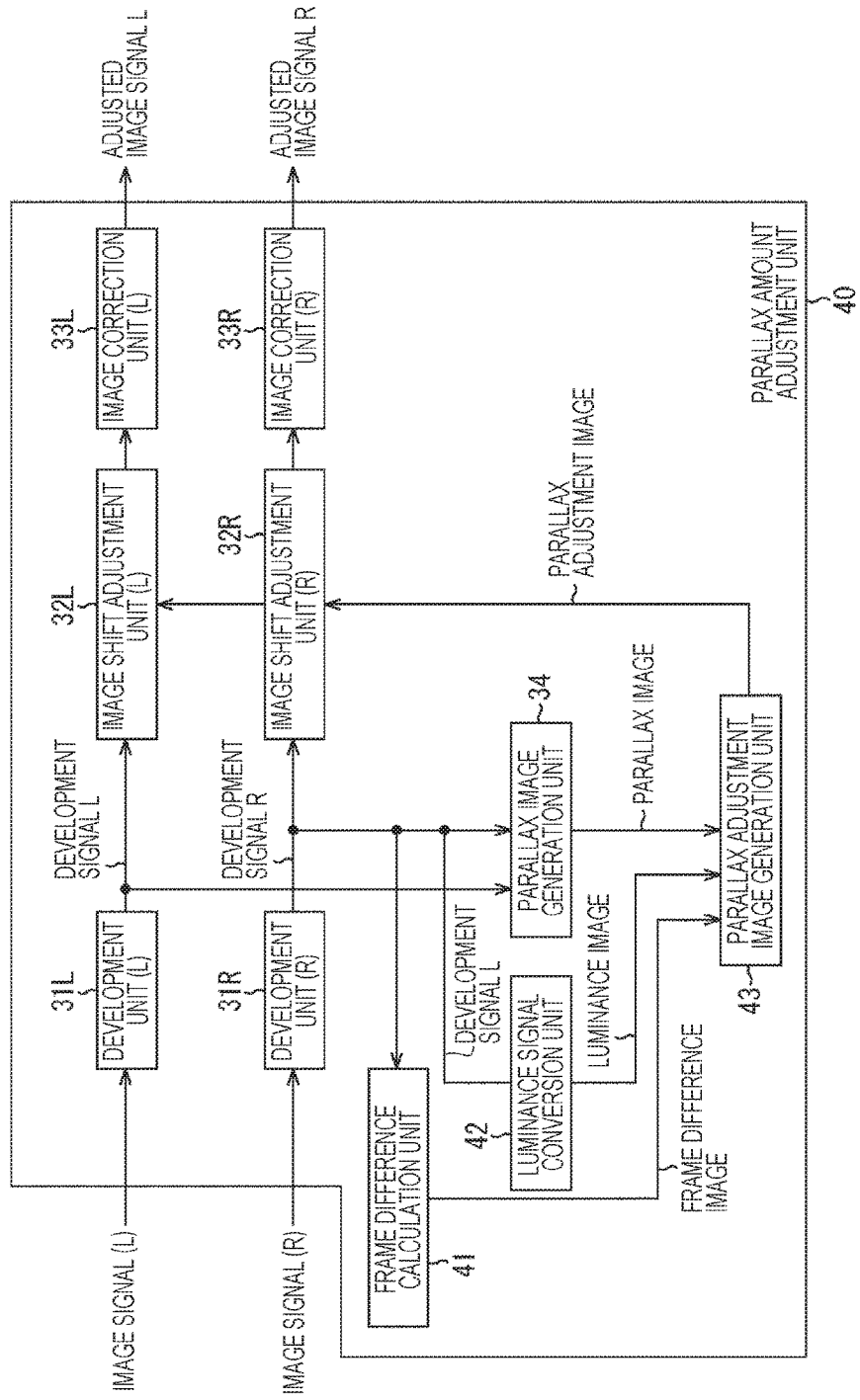
FIG. 10 is a block diagram showing an example configuration of a parallax amount adjustment unit 40.

FIG. 10 is a block diagram showing an example configuration of the parallax amount adjustment unit 40 shown in FIG. 9.

Note that, in the drawing, the components equivalent to those of the parallax amount adjustment unit 12 in FIG. 3 are denoted by the same reference numerals as those used in FIG. 3, and explanation thereof is not repeated herein.

In FIG. 10, the parallax amount adjustment unit 40 is the same as the parallax amount adjustment unit 12 in FIG. 3 in including development units 31L and 31R, image shift adjustment units 32L and 32R, image correction units 33L and 33R, and a parallax image generation unit 34.

However, the parallax amount adjustment unit 40 in FIG. 10 differs from the parallax amount adjustment unit 12 in FIG. 3 in that the parallax adjustment image generation unit 35 is replaced with a parallax adjustment image generation unit 43. Also, the parallax amount adjustment unit 40 in FIG. 10 differs from the parallax amount adjustment unit 12 in FIG. 3 in further including a frame difference calculation unit 41 and a luminance signal conversion unit 42.

Either (the development signal L of) a left-eye image obtained by the development unit 31L or (the development signal R of) a right-eye image obtained by the development unit 31R is supplied to the frame difference calculation unit 41 and the luminance signal conversion unit 42.

In FIG. 10, between the left-eye image and the right-eye image, the left-eye image serving as a reference in generating a parallax image is supplied to the frame difference calculation unit 41 and the luminance signal conversion unit 42, for example.

The frame difference calculation unit 41 calculates an absolute difference value of the pixel value of each pixel between adjacent frames in the left-eye image supplied from the development unit 31L, and supplies the parallax adjustment image generation unit 43 with a frame difference image having the absolute difference value as a pixel value.

The luminance signal conversion unit 42 calculates a luminance signal of each pixel in the left-eye image from the development signal L of the respective planes of R, G, and B in the left-eye image supplied from the development unit 31L, and supplies the parallax adjustment image generation unit 43 with a luminance image having the luminance signal as a pixel value.

The luminance signal can be calculated from the values of R, G, and B as the development signal L, according to an expression (5).

$$Y=0.2126R+0.7152G+0.0722B \quad (5)$$

The frame difference image is supplied from the frame difference calculation unit 41 to the parallax adjustment image generation unit 43, and the luminance image is supplied from the luminance signal conversion unit 42 to the parallax adjustment image generation unit 43. Further, a parallax image is supplied from the parallax image generation unit 34 to the parallax adjustment image generation unit 43.

In accordance with the frame difference image from the frame difference calculation unit 41 and the luminance image from the luminance signal conversion unit 42, the parallax adjustment image generation unit 43 generates a parallax adjustment image, using the parallax image from the parallax image generation unit 34.

Specifically, the absolute difference value that is the pixel value in a position (x, y) in the frame difference image is expressed as S(x, y), and the luminance (signal) that is the pixel value in the position (x, y) in the luminance image is expressed as L(x, y).

According to an expression (6), an expression (7), and an expression (8), for example, the parallax adjustment image generation unit 43 determines the parallax adjustment value c(x, y) by using a parallax amount d(x, y) that is the pixel value of the parallax image. The parallax adjustment image generation unit 43 then generates a parallax adjustment image having the parallax adjustment value c(x, y) as a pixel value, and supplies the parallax adjustment image to the image shift adjustment units 32L and 32R.

$$c(x,y)=(d(x,y)-d(x,y)/a(x,y))/2 \quad (6)$$

$$\text{if } (c(x,y)<0)\{c(x,y)=0\} \quad (7)$$

$$a(x,y)=b \cdot L(x,y) \cdot S(x,y) \quad (8)$$

It should be noted that, in the expression (8), "b" is an adjustment value for adjusting a(x, y), and the value thereof is experimentally determined by the developer of the endoscope system, for example.

With the expressions (6) through (8), the parallax adjustment value c(x, y) is determined according to the expression (6). However, if the parallax adjustment value c(x, y) determined according to the expression (6) is a negative value, the parallax adjustment value c(x, y) is corrected to 0 according to the expression (7).

The parallax adjustment value c(x, y) according to the expression (6) is determined with the use of the parallax amount d(x, y) and a (x, y), and a (x, y) is determined according to the expression (8) using the absolute difference value S(x, y) and the luminance L(x, y). Accordingly, the parallax adjustment value c(x, y) according to the expression (6) can be regarded as a value corresponding to the parallax amount d(x, y) and the absolute difference value (movement) S(x, y). Further, the parallax adjustment value c(x, y) according to the expression (6) can be regarded as a value corresponding to the parallax amount d(x, y) and the luminance L(x, y).

According to the expressions (6) through (8), a pixel with a large absolute difference value S(x, y) and a large luminance L(x, y) is large in a (x, y), and accordingly, the parallax adjustment value c(x, y) is also large. As a result, for a pixel with a large absolute difference value S(x, y) and a large luminance L(x, y), the image shift adjustment units 32L and 32R make adjustments so as to reduce the parallax to a smaller value.

Here, the absolute difference value S(x, y) that is the pixel value of a pixel in the frame difference image indicates movement at the pixel. Meanwhile, mist or smoke generated due to usage of the electrical scalpel 14 characteristically move in a fluid-like manner, is close to white in color, and is high in luminance level. Therefore, in a 3D endoscopic image, a pixel with a large absolute difference value S (x, y) and a large luminance L(x, y) can be regarded as a pixel in a region where mist or smoke appears.

Also, in a 3D endoscopic image, the user viewing the 3D endoscopic image feels discomfort from the region where mist or smoke appears, due to the active movement of the mist or smoke. Therefore, such a region can be regarded as a burdening region that puts a burden on the user.

As described above, in a 3D endoscopic image, a region where mist or smoke appears is a burdening region, and has a large absolute difference value S(x, y) and a large luminance L(x, y).

For a pixel having a large absolute difference value S(x, y) and a large luminance L(x, y), the parallax adjustment image generation unit 35 determines a parallax adjustment value c(x, y) of a large value, and as a result, the image shift adjustment units 32L and 32R conduct adjustment so as to reduce the parallax amount to a smaller value, as described above.

Accordingly, in the 3D endoscopic image, the parallax of the burdening region showing mist or smoke generated due to usage of the electrical scalpel 14 becomes smaller, and the burden on the user can be reduced.

It should be noted that, in the above described case, the parallax amount of a burdening region is adjusted in accordance with both the absolute difference value S(x, y) indicating movement and the luminance L(x, y). However, the parallax amount of a burdening region can be adjusted in accordance with either the absolute difference value S(x, y) or the luminance L(x, y).

Specifically, L(x, y) is set at 1 in the expression (8), so that the parallax amount of the burdening region can be adjusted in accordance with the absolute difference value S(x, y) indicating movement. Alternatively, S(x, y) is set at 1 in the expression (8), so that the parallax amount of the burdening region can be adjusted in accordance with the luminance L(x, y).

Here, in the above expressions (6) through (8), a(x, y) indicates a level at which the pixel in a position (x, y) in (the left-eye image of) a 3D endoscopic image is located in a burdening region where mist or smoke or the like appears (this level will be hereinafter also referred to as the burdening region level). Then, the parallax amount of a pixel with a higher burdening region level a(x, y) is adjusted to a smaller value.

The parallax amount adjustment unit 40 adjusts a parallax amount in accordance with the burdening region level a(x, y) of the pixel as described above. The parallax amount adjustment unit 40 can also detect a burdening region by performing threshold processing, for example, and adjust only the parallax amount of the burdening region.

Specifically, in the parallax amount adjustment unit 40, the parallax adjustment image generation unit 43 can determine the parallax adjustment value c(x, y) according to an expression (9), for example.

$$\text{if } (L(x,y) > \text{TH1 \& } S(x,y) > \text{TH2}) \{c(x,y) = (d(x,y) - d(x,y)/a)/2\} \text{ else } \{c(x,y) = 0\} \quad (9)$$

In the expression (9), TH1 and TH2 are the threshold values to be used in detecting a burdening region, and "a" is a constant equal to or greater than 1. The values of TH1, TH2, and "a" are experimentally determined by the developer of the endoscope system, for example.

According to the expression (9), in a case where the luminance L(x, y) is greater than the threshold value TH1, and the absolute difference value S(x, y) is greater than the threshold value TH2, the pixel in the position (x, y) in (the left-eye image of) the 3D endoscopic image is detected as (a pixel forming) a burdening region in which a predetermined object putting a burden on the user, such as mist or smoke, appears. Then, the parallax adjustment value c(x, y) of the burdening region is determined to be a value ((d(x, y)−d(x, y)/a)/2) corresponding to the parallax amount d(x, y), as in the case with the expression (1).

Also, according to the expression (9), in a case where the luminance L(x, y) is not greater than the threshold value TH1, or the absolute difference value S(x, y) is not greater than the threshold value TH2, the pixel in the position (x, y) in the 3D endoscopic image is determined not to be a burdening region, and the parallax adjustment value c(x, y) is determined to be 0.

Thus, according to the expression (9), the parallax of a burdening region in which mist or smoke or the like appears is adjusted to a smaller value in a 3D endoscopic image. Consequently, the burden on the user can be reduced.

Figure 11:
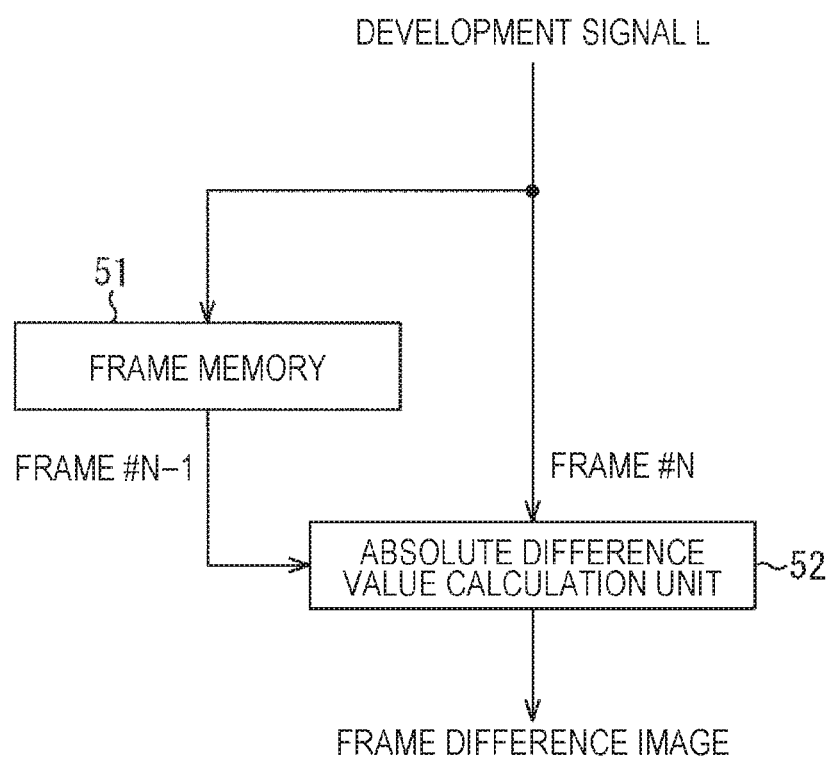
FIG. 11 is a block diagram showing an example configuration of a frame difference calculation unit 41.

FIG. 11 is a block diagram showing an example configuration of the frame difference calculation unit 41 shown in FIG. 10.

In FIG. 11, the frame difference calculation unit 41 includes a frame memory 51 and an absolute difference value calculation unit 52.

The development unit 31L supplies (the development signal L of) the frames of the left-eye image to the frame memory 51 and the absolute difference value calculation unit 52.

The frame memory 51 stores the frames of the left-eye image from the development unit 31L.

The absolute difference value calculation unit 52 sequentially selects each frame of the left-eye image supplied from the development unit 31L as a target frame, and calculates an absolute difference value of the pixel value of each pixel between the target frame and the frame that is located immediately before the target frame and is stored in the frame memory 51. The absolute difference value calculation unit 52 then generates a frame difference image having the absolute difference value as a pixel value, and supplies the frame difference image to the parallax adjustment image generation unit 43.

Specifically, where the current target frame is the Nth frame #N, the absolute difference value calculation unit 52 generates a frame difference image by calculating an absolute difference value of the pixel value of each pixel between the (N−1)th frame #N−1 and the frame #N stored in the frame memory 51.

Next, an image display process to be performed to display a 3D endoscopic image in the endoscope system in FIG. 9 is described.

In the endoscope system shown in FIG. 9, an image display process similar to that in the case described above with reference to the flowchart in FIG. 5 is performed. However, in the image display process in FIG. 5, the process to be performed in step S2 to adjust the parallax amount of a 3D endoscopic image differs from that in the case shown in FIG. 6.

Figure 12:
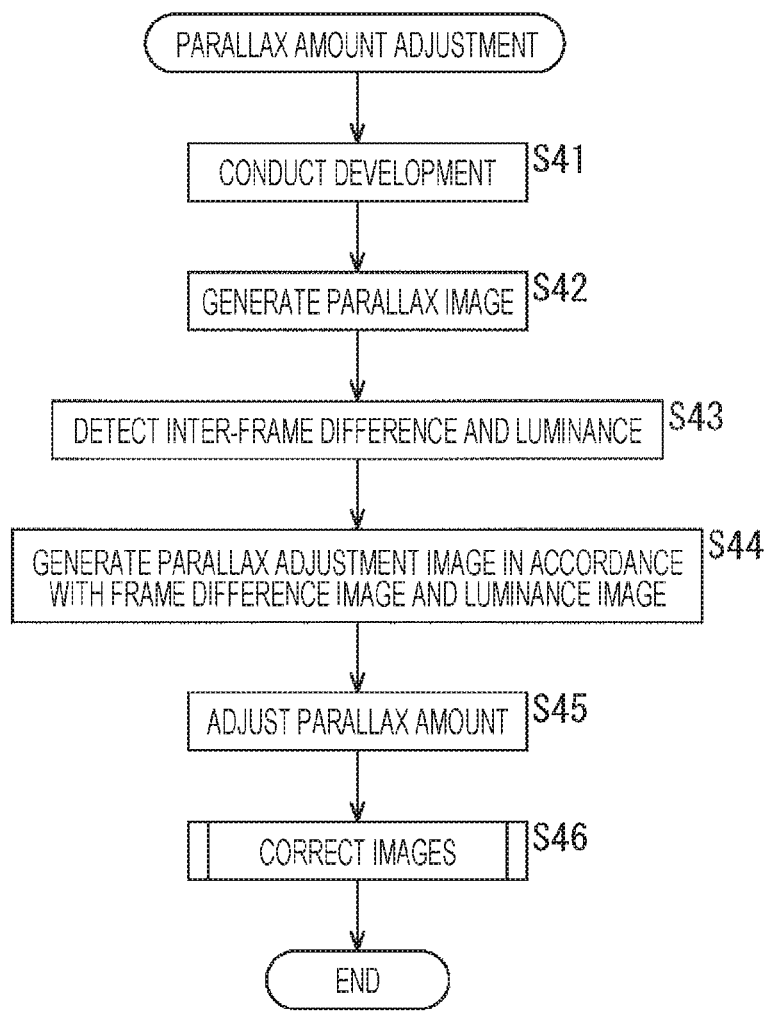
FIG. 12 is a flowchart for explaining an example of a process of adjusting the parallax amount of a 3D endoscopic image.

FIG. 12 is a flowchart for explaining an example of the process to be performed in step S2 in FIG. 5 to adjust the parallax amount of a 3D endoscopic image in the endoscope system shown in FIG. 9.

In step S41, the development units 31L and 31R perform a development process, and the process moves on to step S42.

Specifically, the development unit 31L performs a development process on the image signal L of the left-eye image forming the 3D endoscopic image supplied from the endoscope 11, to generate a development signal L. The development unit 31L supplies the development signal L to the image shift adjustment unit 32L, the parallax image generation unit 34, the frame difference calculation unit 41, and the luminance signal conversion unit 42.

The development unit 31R performs a development process on the image signal R of the right-eye image forming the 3D endoscopic image supplied from the endoscope 11, to generate a development signal R. The development unit 31R supplies the development signal R to the image shift adjustment unit 32R and the parallax image generation unit 34.

In step S42, using the left-eye image from the development unit 31L and the right-eye image from the development unit 31R, the parallax image generation unit 34 generates a parallax image having a parallax amount d(x, y) as a pixel value, and supplies the parallax image to the parallax adjustment image generation unit 43. The process then moves on to step S43.

In step S43, the frame difference calculation unit 41 calculates an absolute difference value of the pixel value of each pixel between adjacent frames in the left-eye image supplied from the development unit 31L, and generates a frame difference image having the absolute difference value as a pixel value. The frame difference calculation unit 41 supplies the frame difference image to the parallax adjustment image generation unit 43.

Further, in step S43, from the left-eye image supplied from the development unit 31L, the luminance signal conversion unit 42 calculates a luminance signal of each pixel in the left-eye image, and generates a luminance image having the luminance signal as a pixel value. The luminance signal conversion unit 42 supplies the luminance image to the parallax adjustment image generation unit 43.

The process then advances from step S43 to step S44. In accordance with the frame difference image from the frame difference calculation unit 41 and the luminance image from the luminance signal conversion unit 42, the parallax adjustment image generation unit 43 generates a parallax adjustment image having the parallax adjustment value c(x, y) as a pixel value, using the parallax image supplied from the parallax image generation unit 34.

The parallax adjustment image generation unit 43 further supplies the parallax adjustment image to the image shift adjustment units 32L and 32R, and the process advances from step S44 to step S45.

Thereafter, in steps S45 and S46, processing similar to that in steps S14 and S15 in FIG. 6 is performed.

Third Embodiment of an Endoscope System

Figure 13:
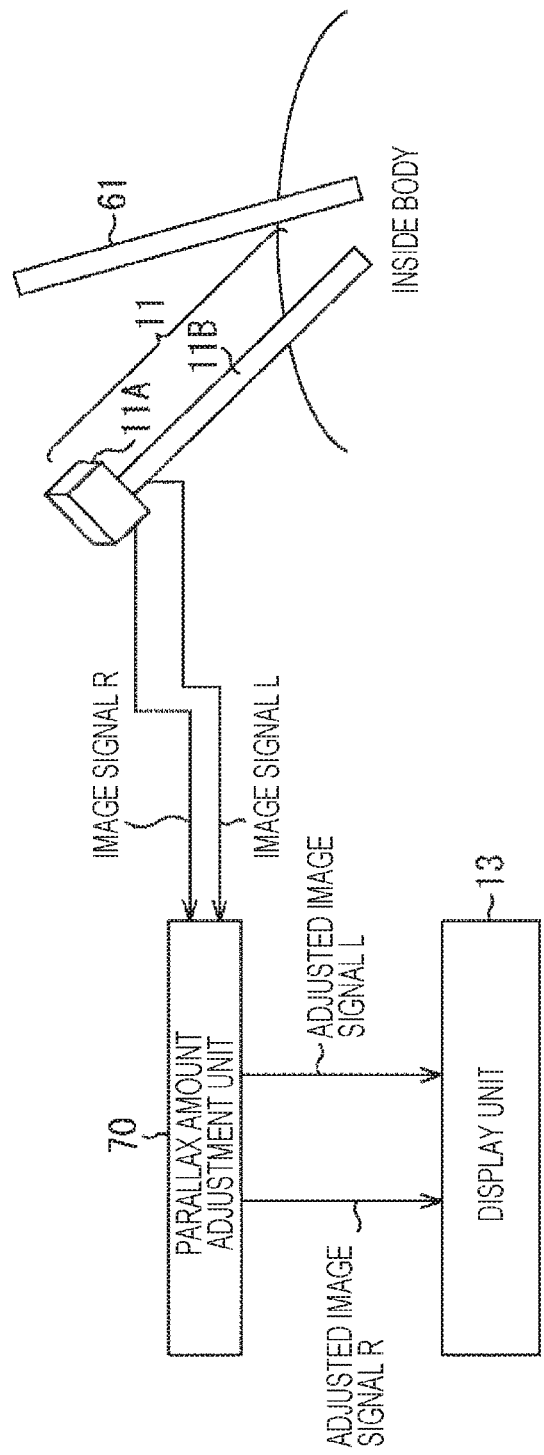
FIG. 13 is a block diagram showing an example configuration of a third embodiment of an endoscope system to which the present technology is applied.

FIG. 13 is a block diagram showing an example configuration of a third embodiment of an endoscope system to which the present technology is applied.

Note that, in the drawing, the components equivalent to those in FIG. 1 are denoted by the same reference numerals as those used in FIG. 1, and explanation thereof will not be repeated below.

In FIG. 13, the endoscope system is the same as that shown in FIG. 1 in including an endoscope 11 and a display unit 13.

However, the endoscope system in FIG. 13 differs from that shown in FIG. 1 in that the electrical scalpel 14, the electrical scalpel switch 15, and the electrical scalpel control unit 16 are replaced with forceps 61.

Further, the endoscope system in FIG. 13 differs from that shown in FIG. 1 in that the parallax amount adjustment unit 12 is replaced with a parallax amount adjustment unit 70.

The forceps 61 are inserted into the body of a patient by a user, and are used in a procedure to be carried out on a target site, for example.

In a case where the parallax of a 3D endoscopic image supplied from the endoscopic image 11 is going to put a burden on the user to view the endoscopic image, the parallax amount adjustment unit 70, like the parallax amount adjustment unit 12 in FIG. 1, adjusts the parallax amount of the 3D endoscopic image so as to reduce the burden on the user, and supplies the adjusted endoscopic image to the display unit 13.

However, unlike the parallax amount adjustment unit 12 that adjusts a parallax amount in accordance with electrical scalpel control information, the parallax amount adjustment unit 70 detects a burdening region where the parallax of a 3D endoscopic image supplied from the endoscopic image 11 becomes a burden, in accordance with the 3D endoscopic image, and adjusts the parallax amount of the burdening region.

It should be noted that, although the parallax amount adjustment unit 40 in FIG. 9 detects burdening region that is a region where mist or smoke appears in a 3D endoscopic image, the parallax amount adjustment unit 70 in FIG. 13 detects a burdening region that is a region where a procedure tool, such as the forceps 61, appears in a 3D endoscopic image.

Specifically, in a 3D endoscopic image, a forceps region that is a region where the forceps 61 appear may extend over a large area from the front side to the target site located in the back, for example. In such a case, when the front-side region with a larger area in the forceps region actively moves due to the user handling the forceps 61, the active movement might make the user feel discomfort, resulting in putting a burden on the user, like the above described mist or smoke with active movement.

Therefore, the parallax amount adjustment unit 70 detects part of or the entire forceps region as a burdening region, and makes adjustments so as to reduce the parallax of the burdening region. Thus, the burden on the user is reduced.

It should be noted that the parallax amount adjustment unit 70 may detect the entire forceps region as a burdening region, or may detect only the front-side region that will put a large burden on the user in a case of moving, as a burdening region in the forceps region.

Figure 14:
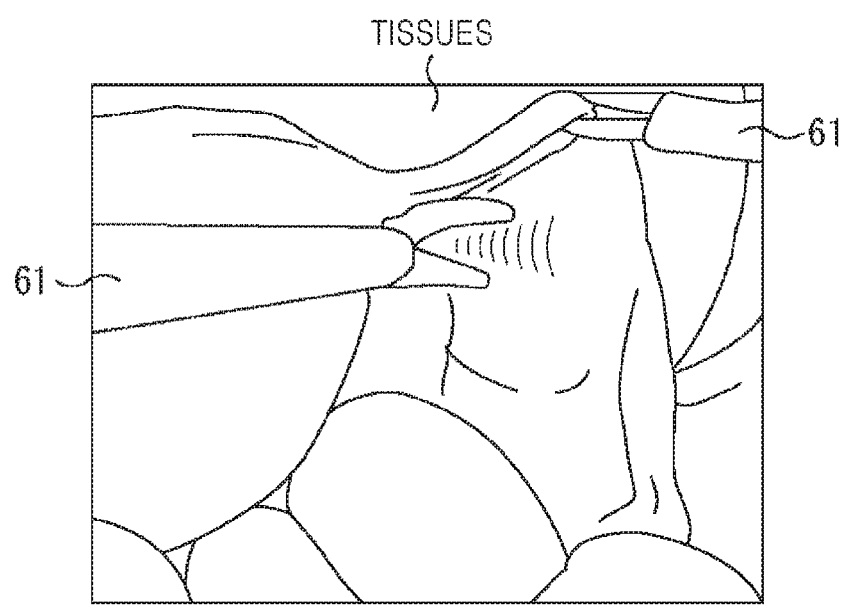
FIG. 14 is a view of an example 3D endoscopic image showing forceps 61.

FIG. 14 is a diagram showing an example of (the left-eye image or the right-eye image forming) a 3D endoscopic image showing the forceps 61.

In FIG. 14, two pairs of forceps as the forceps 61 inserted into a body cavity are shown in the left side and the right side in a 3D endoscopic image, with body tissues being shown in the background.

In the 3D endoscopic image in FIG. 14, the forceps 61 on the left side are shown over a large area from the front side to the target site in the back. In such a 3D endoscopic image, if the forceps region showing the forceps 61 on the left side, or particularly, the front-side region with a large area in the forceps region actively moves, the user viewing the 3D endoscopic image feels discomfort, and a burden is put on the user.

Figure 15:
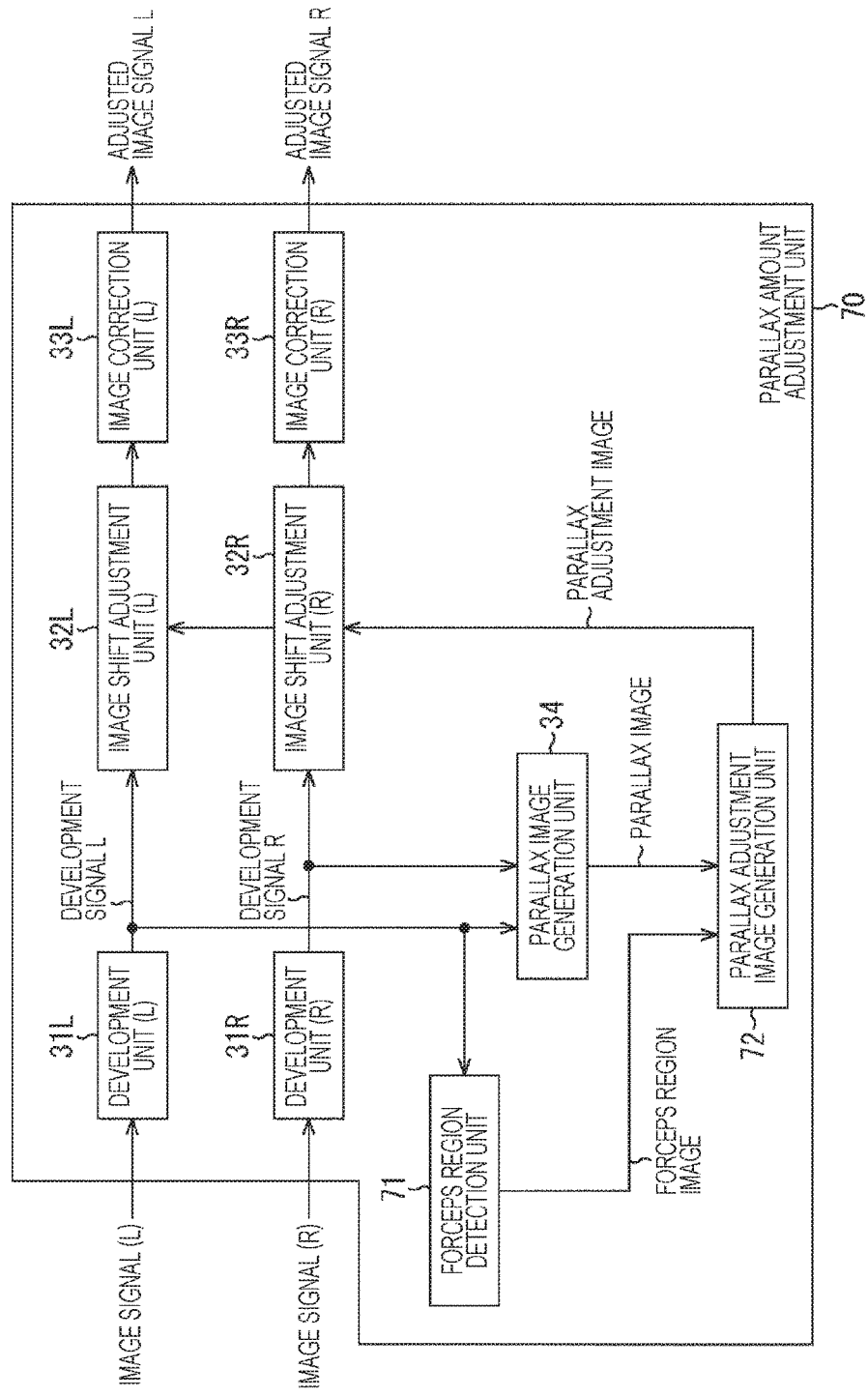
FIG. 15 is a block diagram showing an example configuration of a parallax amount adjustment unit 70.

FIG. 15 is a block diagram showing an example configuration of the parallax amount adjustment unit 70 shown in FIG. 13.

Note that, in the drawing, the components equivalent to those of the parallax amount adjustment unit 12 in FIG. 3 are denoted by the same reference numerals as those used in FIG. 3, and explanation thereof is not repeated herein.

In FIG. 15, the parallax amount adjustment unit 70 is the same as the parallax amount adjustment unit 12 in FIG. 3 in including development units 31L and 31R, image shift adjustment units 32L and 32R, image correction units 33L and 33R, and a parallax image generation unit 34.

However, the parallax amount adjustment unit 70 in FIG. 15 differs from the parallax amount adjustment unit 12 in FIG. 3 in that the parallax adjustment image generation unit 35 is replaced with a parallax adjustment image generation unit 72. Also, the parallax amount adjustment unit 70 in FIG. 15 differs from the parallax amount adjustment unit 12 in FIG. 3 in further including a forceps region detection unit 71.

Either (the development signal L of) a left-eye image obtained by the development unit 31L or (the development signal R of) a right-eye image obtained by the development unit 31R is supplied to the forceps region detection unit 71.

In FIG. 15, between the left-eye image and the right-eye image, the left-eye image serving as a reference in generating a parallax image is supplied to the forceps region detection unit 71, for example.

From the left-eye image supplied from the development unit 31L, the forceps region detection unit 71 detects the forceps region showing the forceps 61, and generates a forceps region image indicating the detection result. The forceps region detection unit 71 supplies the forceps region image to the parallax adjustment image generation unit 72.

Here, the method of detecting the forceps region at the forceps region detection unit 71 is not limited to any particular method. For example, a first detection method or a second detection method can be employed as the method of detecting the forceps region.

By the first detection method, on the assumption that the color of the forceps 61 clearly differs from the color of the body tissues, a hue is calculated from the respective values of R, G, and G in the development signal L of the left-eye image. Threshold processing is then performed on the hue, so that the region in the color of the forceps 61 is detected as the forceps region.

By the second detection method, the luminance of each pixel is determined from the respective values of R, G, and G in the development signal L of the left-eye image, and a luminance image having the luminance as a pixel value is generated. Further, edge detection is performed on the luminance image, so that an edge image indicating the edge is generated. Hough transform is then performed on the edge image, so that (the edge in) straight lines in the edge image are detected. Then, from among the straight lines in the edge image, the longest two straight lines are detected, and the region surrounded by the two straight lines is detected as the forceps region.

Not only the forceps region image from the forceps region detection unit 71, but also the parallax image from the parallax image generation unit 34 is supplied to the parallax adjustment image generation unit 72.

In accordance with the forceps region image supplied from the forceps region detection unit 71, the parallax adjustment image generation unit 72 generates a parallax adjustment image, using the parallax image supplied from the parallax image generation unit 34. The parallax adjustment image generation unit 72 supplies the parallax adjustment image to the image shift adjustment units 32L and 32R.

Specifically, in a case where the pixel in the position (x, y) is (a pixel) in the forceps region, and the parallax d(x, y) of the pixel in the position (x, y) is greater than a threshold value TH3, the parallax adjustment image generation unit 72 determines the parallax adjustment value c(x, y) according to an expression (10), for example.

$$c(x,y) = (d(x,y) - d(x,y)/a(x,y))/2 \quad (10)$$

In addition, in a case where the pixel in the position (x, y) is not in the forceps region, or where the parallax d(x, y) of the pixel in the position (x, y) is not greater than the threshold value TH3 though the pixel in the position (x, y) is in the forceps region, the parallax adjustment image generation unit 72 determines the parallax adjustment value c(x, y) according to an expression (11), for example.

$$c(x,y) = 0 \quad (11)$$

As described above, the parallax adjustment image generation unit 72 determines the parallax adjustment value c(x, y) according to the expression (10) or (11), and generates a parallax adjustment image having the parallax adjustment value c(x, y) as a pixel value. The parallax adjustment image generation unit 72 supplies the parallax adjustment image to the image shift adjustment units 32L and 32R.

It should be noted that the threshold value TH3 is the threshold value to be used in detecting a burdening region, and "a" is a constant equal to or greater than 1. The values of TH3 and "a" are experimentally determined by the developer of the endoscope system, for example.

The parallax adjustment image generation unit 72 described above detects a burdening region that is a region in which the parallax d(x, y) is greater than the threshold value TH3, or a front-side region, in the forceps region showing the forceps 61 as a predetermined object. Then, the parallax adjustment value c(x, y) of the burdening region is determined to be a value ((d(x, y)–d(x, y)/a)/2) corresponding to the parallax amount d(x, y), as in the case with the expression (1), for example.

In addition, in a case where the pixel in the position (x, y) is not in the forceps region, or where the parallax d(x, y) of the pixel in the position (x, y) is not greater than the threshold value TH3 though the pixel in the position (x, y) is in the forceps region, the parallax adjustment image generation unit 72 determines the pixel in the position (x, y) not to be in a burdening region, and determines the parallax adjustment value c(x, y) to be 0.

Accordingly, the image shift adjustment units 32L and 32R adjust the parallax, in accordance with (the parallax adjustment image having a pixel value that is) the parallax adjustment value c(x, y) determined by the parallax adjustment image generation unit 72. Thus, the burden on the user can be reduced.

Specifically, the image shift adjustment units 32L and 32R adjust the parallax of the burdening region on the front side in the forceps region showing the forceps 61 in the 3D endoscopic image. As a result, the burden on the user can be reduced.

FIGS. 16A and 16B show a view of an example forceps region image generated by the forceps region detection unit 71 in FIG. 15.

FIG. 16A shows an example left-eye image as the current object image from which a forceps region is to be detected by the forceps region detection unit 71.

In the left-eye image in FIG. 16A, the forceps 61 appear, extending from the center of the left-eye image toward the bottom.

FIG. 16B shows an example forceps region image generated by detecting the forceps region from the left-eye image shown in FIG. 16A.

The forceps region image is a binary image indicating the forceps region, for example.

Next, an image display process to be performed to display a 3D endoscopic image in the endoscope system in FIG. 13 is described.

In the endoscope system shown in FIG. 13, an image display process similar to that in the case described above with reference to the flowchart in FIG. 5 is performed. However, in the image display process in FIG. 5, the process to be performed in step S2 to adjust the parallax amount of a 3D endoscopic image differs from that in the case shown in FIG. 6.

Figure 17:
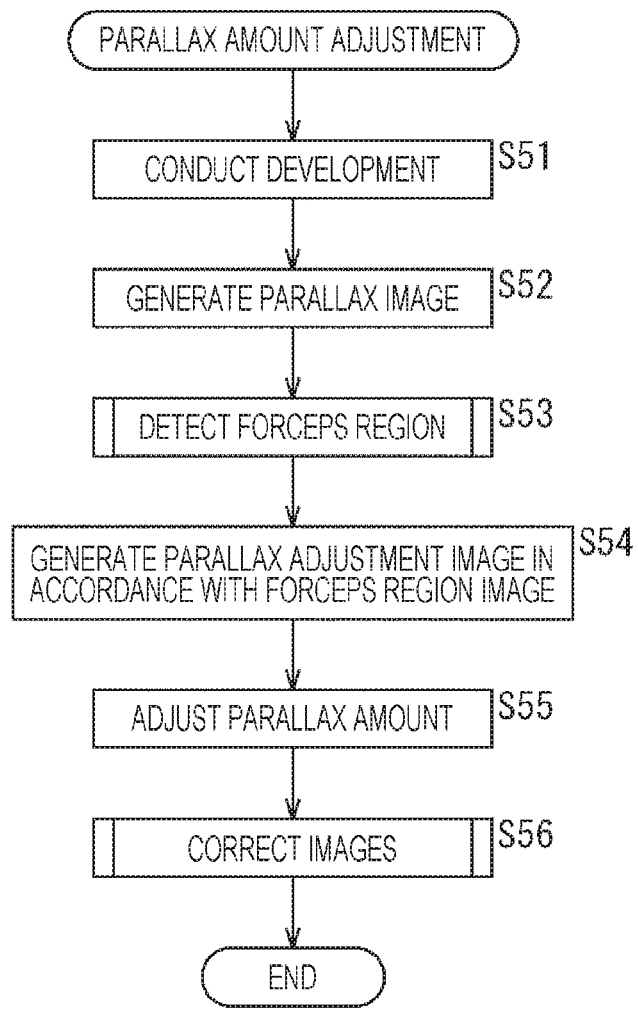
FIG. 17 is a flowchart for explaining an example of a process of adjusting the parallax amount of a 3D endoscopic image.

FIG. 17 is a flowchart for explaining an example of the process to be performed in step S2 in FIG. 5 to adjust the parallax amount of a 3D endoscopic image in the endoscope system shown in FIG. 13.

In step S51, the development units 31L and 31R perform a development process, and the process moves on to step S52.

Specifically, the development unit 31L performs a development process on the image signal L of the left-eye image forming the 3D endoscopic image supplied from the endoscope 11, to generate a development signal L. The development unit 31L supplies the development signal L to the image shift adjustment unit 32L, the parallax image generation unit 34, and the forceps region detection unit 71.

The development unit 31R performs a development process on the image signal R of the right-eye image forming the 3D endoscopic image supplied from the endoscope 11, to generate a development signal R. The development unit 31R supplies the development signal R to the image shift adjustment unit 32R and the parallax image generation unit 34.

In step S52, using the left-eye image from the development unit 31L and the right-eye image from the development unit 31R, the parallax image generation unit 34 generates a parallax image having a parallax amount d(x, y) as a pixel value, and supplies the parallax image to the parallax adjustment image generation unit 72. The process then moves on to step S53.

In step S53, the forceps region detection unit 71 performs a forceps region detection process to detect the forceps region from the left-eye image supplied from the development unit 31L, and generates a forceps region image indicating the forceps region. The forceps region detection unit 71 supplies the forceps region image to the parallax adjustment image generation unit 72.

The process then advances from step S53 to step S54. In accordance with the forceps region image supplied from the forceps region detection unit 71, the parallax adjustment image generation unit 72 generates a parallax adjustment image having a parallax adjustment value c(x, y) as a pixel value, using the parallax image supplied from the parallax image generation unit 34.

The parallax adjustment image generation unit 72 further supplies the parallax adjustment image to the image shift adjustment units 32L and 32R, and the process advances from step S54 to step S55.

Thereafter, in steps S55 and S56, processing similar to that in steps S14 and S15 in FIG. 6 is performed.

Figure 18:
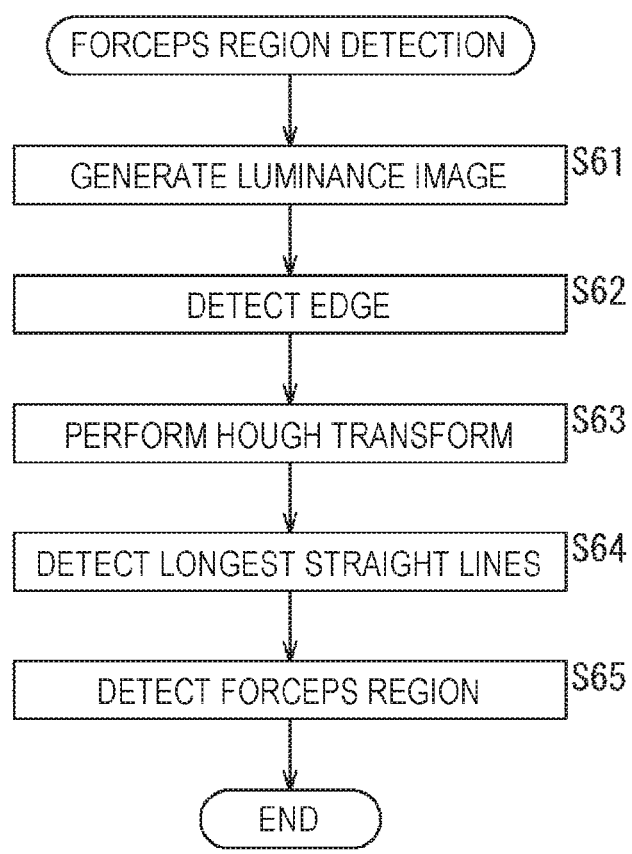
FIG. 18 is a flowchart for explaining an example of a forceps region detection process.

FIG. 18 is a flowchart for explaining an example of the forceps region detection process to be performed in step S53 in FIG. 17.

The forceps region detection unit 71 detects a forceps region from the left-eye image by one of the above described first and second detection methods, or by the second detection method, for example.

Specifically, in step S61, the forceps region detection unit 71 determines the luminance of each pixel from the respective values of R, G, and G in the development signal L of the left-eye image supplied from the development unit 31L, and generates a luminance image having the luminance as a pixel value. The process then moves on to step S62.

In step S62, the forceps region detection unit 71 performs edge detection on the luminance image, and generates an edge image indicating the edge. The process then moves on to step S63.

In step S63, the forceps region detection unit 71 detects straight lines (line segments) in the edge image by performing Hough transform on the edge image. The process then moves on to step S64.

In step S64, from among the straight lines detected in step S63 from the edge image, the forceps region detection unit 71 detects the two longest straight lines in descending order as boundary straight lines indicating the boundaries of a forceps region. The process then moves on to step S65.

In step S65, the forceps region detection unit 71 detects a forceps region that is the region surrounded by the two boundary straight lines. The process then comes to an end (returns).

It should be noted that, although the parallax amount adjustment unit 70 in FIG. 13 detects (part of) the forceps region showing the forceps 61 as a burdening region, the parallax amount adjustment unit 70 may detect a burdening region that is part of or all of a region showing a procedure tool other than the forceps 61, such as a sheath, or a predetermined object that puts a burden on the user viewing the 3D endoscopic image (such as an object that actively moves in the depth direction, or a moving object that occupies a large area in the 3D endoscopic image). The parallax amount of the burdening region is then adjusted so as to reduce the burden on the user.

As described above, in a case where a surgical operation is performed while the operator is viewing a 3D endoscopic image, for example, the endoscope system of this embodiment adjusts the parallax amount to cope with actively moving mist or smoke in the vicinity of the tip of the endoscopic scope 11B. Accordingly, a 3D endoscopic image that causes little strangeness or discomfort can be presented to the user (operator).

Further, in a case where a surgical operation is performed while the operator is viewing a 3D endoscopic image, for example, the endoscope system of this embodiment adjusts the parallax amount to cope with an actively moving forceps region in the vicinity of the tip of the endoscopic scope 11B. Accordingly, a 3D endoscopic image that causes little strangeness or discomfort can be presented to the user.

Thus, the endoscope system of this embodiment can alleviate fatigue of the user and contribute to maintenance of concentration.

It should be noted that the present technology can be applied in a case where not only an endoscopic image captured with the endoscope 11 having the endoscopic scope 11B inserted into a human body, but also an endoscopic image captured with a capsule endoscope is processed, for example.

Further, the present technology can be applied in a case where not only an image of a human body but also an image of a living organism other than a human body is processed.

Also, the present technology can be applied in a case where not only an endoscopic image of a living organism imaged with the endoscope 11 but also a biological image of a living organism imaged with a microscope is processed, for example. Furthermore, the present technology can be applied to an endoscopic image of an object imaged with an endoscope called a fiberscope, the object not being a living organism.

Further, the parallax amount adjustments in the endoscope systems of the first through third embodiments described above can be used in combination. That is, adjustments to reduce parallax amounts can be made both in a region where smoke or mist appears and in a forceps region where forceps appear.

<Description of a Computer to which the Present Technology is Applied>

The above described series of processes to be performed by the parallax amount adjustment unit 12, 40, or 70 can be performed with hardware, and can also be performed with software. Where the series of processes are performed with software, the program that forms the software is installed into a microcomputer or the like.

Figure 19:
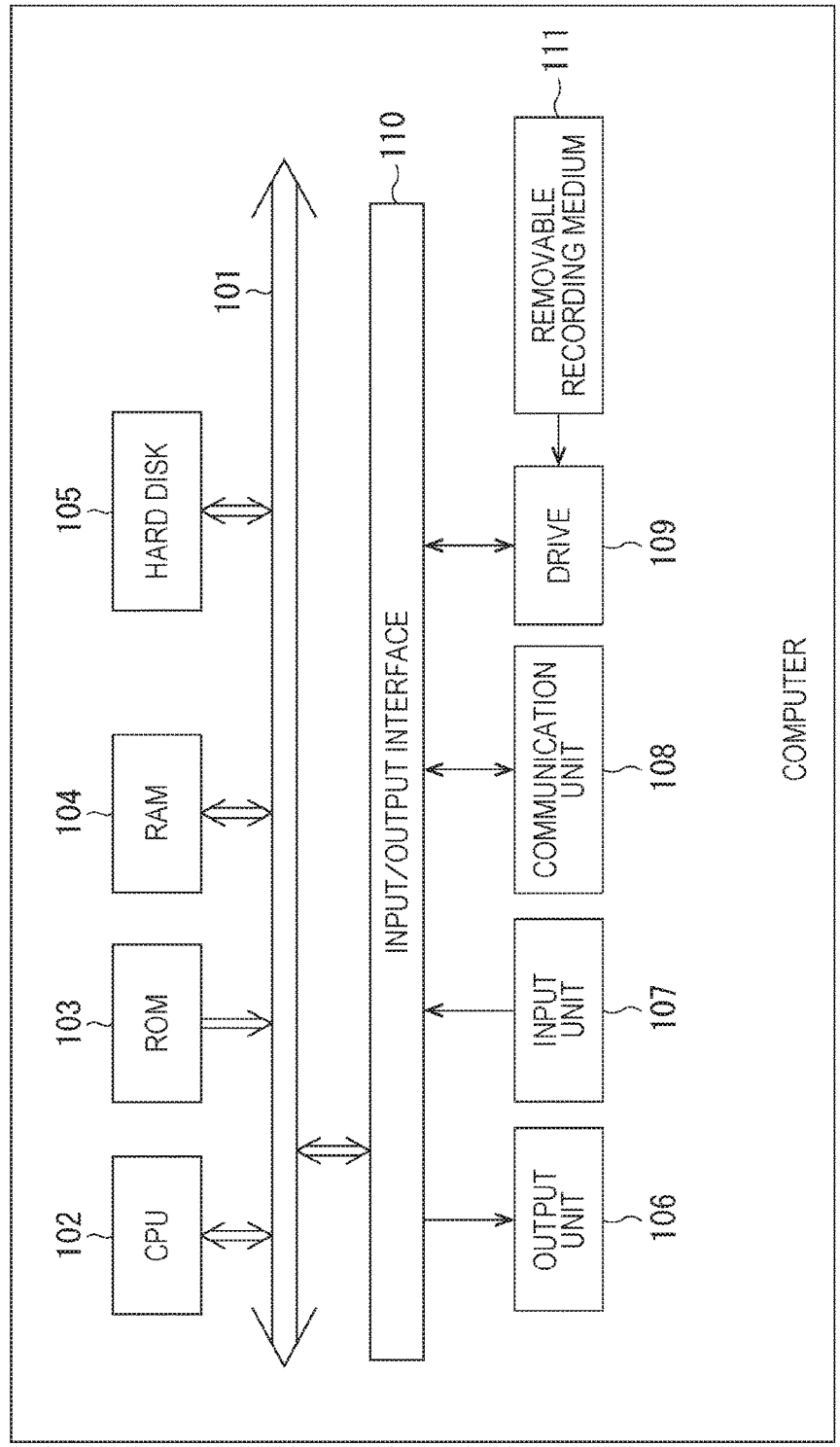
FIG. 19 is a block diagram showing an example configuration of an embodiment of a computer to which the present technology is applied.

In view of this, FIG. 19 shows an example configuration of an embodiment of a computer into which the program for performing the above described series of processes is installed.

The program can be recorded beforehand in a hard disk 105 or a ROM 103 provided as a recording medium in the computer.

Alternatively, the program can be stored (recorded) in a removable recording medium 111. Such a removable recording medium 111 can be provided as so-called packaged software. Here, the removable recording medium 111 may be a flexible disk, a compact disc read only memory (CD-ROM), a magneto-optical (MO) disk, a digital versatile disc (DVD), a magnetic disk, or a semiconductor memory, for example.

Note that, the program can be installed into the computer from the above described removable recording medium 111, but can also be downloaded into the computer via a communication network or a broadcasting network and be installed into the internal hard disk 105. That is, the program can be wirelessly transferred from a download site, for example, to the computer via an artificial satellite for digital satellite broadcasting, or can be transferred by cable to the computer via a network such as a local area network (LAN) or the Internet.

The computer includes a central processing unit (CPU) 102, and an input/output interface 110 is connected to the CPU 102 via a bus 101.

When an instruction is input by a user operating an input unit 107 or the like via the input/output interface 110, the CPU 102 executes the program stored in the read only memory (ROM) 103 in accordance with the instruction. Alternatively, the CPU 102 loads the program stored in the hard disk 105 into a random access memory (RAM) 104, and executes the program.

By doing so, the CPU 102 performs the processes according to the above described flowcharts, or performs the processes with the above described configurations illustrated in the block diagrams. Then, where necessary, the CPU 102 outputs the process results from an output unit 106 or transmit the process results from a communication unit 108, via the input/output interface 110, for example, and further stores the process results into the hard disk 105.

Note that, the input unit 107 is formed with a keyboard, a mouse, a microphone, and the like. In addition, the output unit 106 is formed with a liquid crystal display (LCD), a speaker, and the like.

In this specification, the processes to be performed by the computer in accordance with the program are not necessarily performed in chronological order compliant with the sequences shown in the flowcharts. That is, the processes to be performed by the computer in accordance with the program include processes to be performed in parallel or independently of one another (such as parallel processes or object-based processes).

In addition, the program may be executed by one computer (processor), or may be executed in a distributive manner by more than one computer. Further, the program may be transferred to a remote computer, and be executed therein.

Further, in this specification, a system means an assembly of components (devices, modules (parts), and the like), and not all the components need to be provided in the same housing. In view of this, devices that are housed in different housings and are connected to one another via a network form a system, and one device having modules housed in one housing is also a system.

It should be noted that embodiments of the present technology are not limited to the above described embodiments, and various modifications may be made to them without departing from the scope of the present technology.

For example, the present technology can be embodied in a cloud computing configuration in which one function is shared among devices via a network, and processing is performed by the devices cooperating with one another.

Also, the respective steps described with reference to the above described flowcharts can be carried out by one device or can be shared among devices.

Further, in a case where more than one process is included in one step, the processes included in the step can be performed by one device or can be shared among devices.

In addition, the advantageous effects described in this specification are merely examples, and the advantageous effects of the present technology are not limited to them and may include other effects.

The present technology may also be embodied in the configurations described below.

<1>
An image processing device including
a parallax amount adjustment unit that adjusts the parallax amount of a three-dimensional (3D) biological image of an imaged living organism, depending on whether the parallax of the 3D biological image puts a burden on a user.

<2>
The image processing device of <1>, in which, in a case where an energy device is being used, the parallax amount adjustment unit adjusts the parallax amount of the 3D biological image.

<3>
The image processing device of <2>, in which the energy device is an electrical scalpel.

<4>
The image processing device of <1>, in which, in accordance with the 3D biological image, the parallax amount adjustment unit adjusts the parallax amount of a burdening region where the parallax in the 3D biological image becomes a burden.

<5>
The image processing device of <4>, in which the parallax amount adjustment unit adjusts the parallax amount of the burdening region, in accordance with movement of the 3D biological image.

<6>
The image processing device of <4>, in which the parallax amount adjustment unit adjusts the parallax amount of the burdening region, in accordance with luminance of the 3D biological image.

<7>
The image processing device of <4>, in which the parallax amount adjustment unit adjusts the parallax amount of the burdening region, in accordance with movement and luminance of the 3D biological image.

<8>
The image processing device of <4>, in which the parallax amount adjustment unit detects a region showing a predetermined object as the burdening region in the 3D biological image.

<9>
The image processing device of <8>, in which the parallax amount adjustment unit detects a region showing a procedure tool as the burdening region in the 3D biological image.

<10>
The image processing device of <8>, in which the parallax amount adjustment unit detects a region showing mist or smoke as the burdening region in the 3D biological image.

<11>
The image processing device of any of <1> to <10>, in which the parallax amount adjustment unit adjusts the parallax amount of the 3D biological image, to reduce the parallax.

<12>

The image processing device of <11>, in which the parallax amount adjustment unit adjusts the parallax amount of the 3D biological image, to reduce the parallax by an adjustment value corresponding to the parallax amount.

<13>

The image processing device of <11>, in which the parallax amount adjustment unit adjusts the parallax amount of the 3D biological image, to reduce the parallax by an adjustment value corresponding to the parallax amount and at least one of movement and luminance of the 3D biological image.

<14>

The image processing device of any of <1> to <13>, in which the parallax amount adjustment unit adjusts the parallax amount of the 3D biological image by horizontally shifting the pixel value of a target pixel in one of a left-eye image to be viewed with the left eye and a right-eye image to be viewed with the right eye, and the pixel value of a corresponding pixel corresponding to the target pixel, the corresponding pixel being a pixel in the other one of the left-eye image and the right-eye image, the left-eye image and the right-eye image constituting the 3D biological image.

<15>

The image processing device of <14>, further including an image correction unit that corrects the left-eye image and the right-eye image by interpolating the pixel value of a missing pixel in the left-eye image and the right-eye image, the pixel value of the missing pixel having been missing due to the pixel value shifting.

<16>

The image processing device of <15>, in which the image correction unit interpolates the pixel value of the missing pixel, using the pixel value of one of the pixels located near the missing pixel, the one of the pixels not being a missing pixel.

<17>

The image processing device of any of <1> to <16>, in which the biological image is an endoscopic image formed with an endoscope imaging the living organism.

<18>

An image processing method including
the step of adjusting the parallax amount of a three-dimensional (3D) biological image of an imaged living organism, depending on whether the parallax of the 3D biological image puts a burden on a user.

<19>

A program for causing a computer to function as
a parallax amount adjustment unit that adjusts the parallax amount of a three-dimensional (3D) biological image of an imaged living organism, depending on whether the parallax of the 3D biological image puts a burden on a user.

<20>

An endoscope system including:
an endoscope that captures a three-dimensional (3D) image;
a parallax amount adjustment unit that adjusts the parallax amount of a 3D biological image, depending on whether the parallax of the 3D biological image puts a burden on a user, the 3D biological image being obtained with the endoscope imaging a living organism; and
a display unit that displays the 3D biological image having the parallax amount adjusted by the parallax amount adjustment unit.

REFERENCE SIGNS LIST

11 Endoscope
11A Camera head
11B Endoscopic scope
12 Parallax amount adjustment unit
13 Display unit
14 Electrical scalpel
15 Electrical scalpel switch
16 Electrical scalpel control unit
21L, 21R Imaging element
31L, 31R Development unit
32L, 32R Image shift adjustment unit
33L, 33R Image correction unit
34 Parallax image generation unit
35 Parallax adjustment image generation unit
40 Parallax amount adjustment unit
41 Frame difference calculation unit
42 Luminance signal conversion unit
43 Parallax adjustment image generation unit
51 Frame memory
52 Absolute difference value calculation unit
61 Forceps
70 Parallax amount adjustment unit
71 Forceps region detection unit
101 Bus
102 CPU
103 ROM
104 RAM
105 Hard Disk
106 Output unit
107 Input unit
108 Communication unit
109 Drive
110 Input/output interface
111 Removable recording medium

The invention claimed is:

1. An image processing device, comprising:
circuitry configured to:
generate at least one development signal based on a development process on a three-dimensional (3D) biological image of a living organism;
generate a parallax image of the 3D biological image based on the at least one development signal; and
adjust a parallax amount in the parallax image of the 3D biological image based on whether a parallax of the 3D biological image is greater than a threshold parallax.

2. The image processing device according to claim 1, wherein the parallax amount in the parallax image of the 3D biological image is adjusted based on an usage of an energy device.

3. The image processing device according to claim 2, wherein the energy device is an electrical scalpel.

4. The image processing device according to claim 1, wherein the parallax amount in the parallax image of the 3D biological image is adjusted at a burdening region where the parallax in the 3D biological image is greater than the threshold parallax.

5. The image processing device according to claim 4, wherein the parallax amount of the burdening region is adjusted based on movement of the 3D biological image.

6. The image processing device according to claim 4, wherein the parallax amount of the burdening region is adjusted based on luminance of the 3D biological image.

7. The image processing device according to claim 4, wherein the parallax amount of the burdening region is adjusted based on movement and luminance of the 3D biological image.

8. The image processing device according to claim 4, wherein the circuitry is further configured to detect a region that indicates an object as the burdening region in the 3D biological image.

9. The image processing device according to claim 8, wherein the object is a procedure tool in the 3D biological image.

10. The image processing device according to claim 8, wherein the object is mist or smoke in the 3D biological image.

11. The image processing device according to claim 1, wherein the parallax amount in the parallax image of the 3D biological image is adjusted to reduce the parallax of the 3D biological image.

12. The image processing device according to claim 11, wherein the parallax amount in the parallax image of the 3D biological image is adjusted to reduce the parallax of the 3D biological image based on an adjustment value corresponding to the parallax amount.

13. The image processing device according to claim 11, wherein the parallax amount in the parallax image of the 3D biological image is adjusted to reduce the parallax of the 3D biological image based on at least one of movement or luminance of the 3D biological image.

14. The image processing device according to claim 1, wherein
the parallax amount of the 3D biological image is adjusted based on a horizontal shift of a pixel value of a target pixel in one of a left-eye image to view with a left eye or a right-eye image to view with a right eye,
the pixel value of a corresponding pixel corresponds to the target pixel,
the corresponding pixel is a pixel in an image other than one of the left-eye image or the right-eye image, and
the left-eye image and the right-eye image constitute the 3D biological image.

15. The image processing device according to claim 14, wherein
the circuitry is further configured to correct one of the left-eye image or the right-eye image based on an interpolation of a pixel value of a corresponding missing pixel in one of the left-eye image or the right-eye image, and
the pixel value of the corresponding missing pixel of one of the left-eye image or the right-eye image is based on the horizontal shift of the pixel value of the target pixel in one of the left-eye image or the right-eye image.

16. The image processing device according to claim 15, wherein
the circuitry is further configured to interpolate the pixel value of the corresponding missing pixel of one of the left-eye image or the right-eye image based on a pixel value of a pixel adjacent to the corresponding missing pixel of one of the left-eye image or the right-eye image, and
the pixel is other than the corresponding missing pixel of one of the left-eye image or the right-eye image.

17. The image processing device according to claim 1, wherein
the biological image is an endoscopic image, and
the endoscopic image is based on a capture of an endoscope image of the living organism.

18. An image processing method, comprising
generating at least one development signal based on a development process on a three-dimensional (3D) biological image of a living organism;
generating a parallax image based on the at least one development signal; and
adjusting a parallax amount in the parallax image of the 3D biological image based on whether a parallax of the 3D biological image is greater than a threshold parallax.

19. A non-transitory computer-readable medium having stored thereon, computer-executable instructions, which when executed by a processor of an image processing device, cause the processor to execute operations, the operations comprising:
generating at least one development signal based on a development process on a three-dimensional (3D) biological image of a living organism;
generating a parallax image based on the at least one development signal; and
adjusting a parallax amount in the parallax image of the 3D biological image based on whether a parallax of the 3D biological image is greater than a threshold parallax.

20. An endoscope system, comprising:
an imaging device configured to capture a three-dimensional (3D) biological image of a living organism; and
circuitry configured to:
generate at least one development signal based on a development process on the 3D biological image;
generate a parallax image based on the at least one development signal;
adjust a parallax amount in the parallax image of the 3D biological image based on whether a parallax of the 3D biological image is greater than a threshold parallax; and
control a display device to display the 3D biological image having the adjusted parallax amount.

21. An image processing device, comprising:
circuitry configured to:
generate at least one development signal based on a development process on a three-dimensional (3D) biological image of a living organism;
generate a parallax image of the 3D biological image based on the at least one development signal;
adjust a parallax amount of the parallax image of the 3D biological image based on:
whether a parallax of the 3D biological image is greater than a threshold parallax, and
a horizontal shift of a pixel value of a target pixel in one of a left-eye image to view with a left eye or a right-eye image to view with a right eye; and
control a display device to display the 3D biological image having the adjusted parallax amount.

* * * * *